(12) United States Patent
Barbier et al.

(10) Patent No.: US 6,184,422 B1
(45) Date of Patent: Feb. 6, 2001

(54) CYCLOHEXANEDIOL DERIVATIVES

(75) Inventors: Pierre Barbier, Rixheim (FR); Franz Bauer, Reinach; Peter Mohr, Basel, both of (CH); Marc Muller, Saint-Louis (FR); Wolfgang Pirson, Weil am Rhein (DE)

(73) Assignee: Hoffman-La Roche Inc., Nutley, NJ (US)

( * ) Notice: Under 35 U.S.C. 154(b), the term of this patent shall be extended for 0 days.

(21) Appl. No.: 09/252,508

(22) Filed: Feb. 18, 1999

(30) Foreign Application Priority Data

Feb. 26, 1998 (EP) .................................... 98103346

(51) Int. Cl.[7] .................................... C07C 35/18

(52) U.S. Cl. .................... 568/825; 556/443; 560/231; 568/669; 568/670; 568/828

(58) Field of Search ..................... 568/825, 828, 568/669, 670; 560/231; 556/443

(56) References Cited

U.S. PATENT DOCUMENTS 5,969,190 * 10/1999 Bauer .................... 568/400

FOREIGN PATENT DOCUMENTS

| 0 711 789 | 5/1997 | (EP) . |
| WO 95/01960 | 1/1995 | (WO) . |
| WO 95/19963 | 7/1995 | (WO) . |

OTHER PUBLICATIONS

Perlman, et al., Novel Synthesis of 19-Nor-Vitamin D Compounds, Tetrahedron Letters, vol. 32, No. 52, pp. 7663-7666 (1991).

Brown, et al., The Cyclic Hydroboration of Dienes with Thexylborane, Journal of the American Chemical Society, vol. 94, pp. 3567-3572 (1972).

* cited by examiner

Primary Examiner—Michael L. Shippen
(74) Attorney, Agent, or Firm—George W. Johnston; William H. Epstein; John P. Parise

(57) ABSTRACT

Compounds of formula I

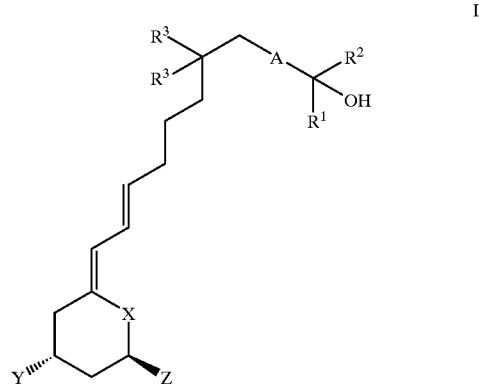

wherein
X is $C=CH_2$ or $CH_2$;
Y and Z are independently of each other hydrogen, fluorine or hydroxy;
A is $-C\equiv C-$, $-CH=CH-$ or $-CH_2-CH_2-$,
$R^1$ and $R^2$ are independently of each other alkyl or perfluoroalkyl; and
$R^3$ is lower alkyl
are useful in the treatment or prevention of hyperproliferative skin diseases, particularly psoriasis, basal cell carcinomas, disorders of keratinization and keratosis; or for reversing the conditions associated with photodamage.

27 Claims, No Drawings

CYCLOHEXANEDIOL DERIVATIVES

BACKGROUND OF THE INVENTION

The present invention relates to cyclohexanediol derivatives for treatment and prevention of hyperproliferative skin diseases and reversing conditions associated with photodamage.

SUMMARY OF THE INVENTION

The invention relates to the novel retiferol derivatives of formula I:

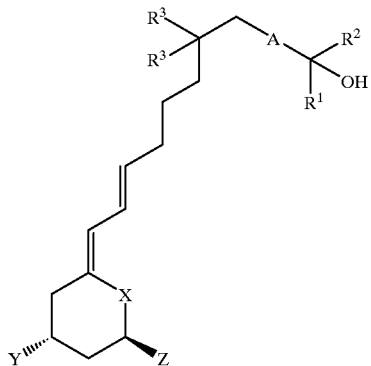

wherein

X is $C=CH_2$ or $CH_2$;

Y and Z are independently of each other hydrogen, fluorine or hydroxy;

A is $—C\equiv C—$, $—CH=CH—$ or $—CH_2—CH_2—$;

$R^1$ and $R^2$ are independently of each other alkyl or perfluoroalkyl; and $R^3$ is lower alkyl.

Compounds of formula I can be utilized to treat or prevent hyperproliferative skin diseases such as psoriasis, basal cell carcinomas, disorders of keratinization and keratosis; neoplastic diseases; disorders of the sebaceous glands such as acne and seborrhoic dermatitis. The compounds of formula I can also be utilized in reversing the conditions associated with photodamage, particularly for the oral or topical treatment of the skin damaged through sun exposure, the effects of wrinkling, elastosis and premature ageing.

The present invention furthermore relates to a process for the preparation of compounds of formula I, pharmaceutical compositions containing such compounds, and the use of these compounds for the treatment and prevention of the above mentioned disorders, and for the manufacture of pharmaceutical compositions for the treatment and prevention of the above mentioned disorders.

DETAILED DESCRIPTION OF THE INVENTION

The invention relates to the novel retiferol derivatives of formula I:

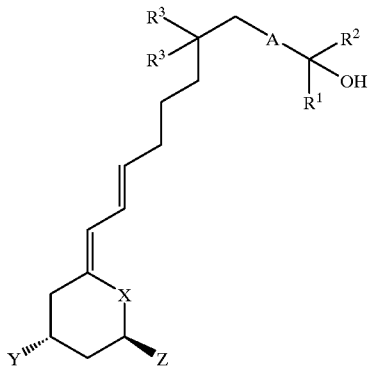

wherein

X is $C=CH_2$ or $CH_2$;

Y and Z are independently of each other hydrogen, fluorine or hydroxy;

A is $—C\equiv C—$, $—CH=CH—$ or $—CH_2—CH_2—$;

$R^1$ and $R^2$ are independently of each other alkyl or perfluoroalkyl; and $R^3$ is lower alkyl.

Compounds of formula I can be utilized to treat or prevent hyperproliferative skin diseases such as psoriasis, basal cell carcinomas, disorders of keratinization and keratosis; neoplastic diseases; disorders of the sebaceous glands such as acne and seborrhoic dermatitis. The compounds of formula I can also be utilized in reversing the conditions associated with photodamage, particularly for the oral or topical treatment of the skin damaged through sun exposure, the effects of wrinkling, elastosis and premature ageing.

The present invention furthermore relates to a process for the preparation of compounds of formula I, pharmaceutical compositions containing such compounds, and the use of these compounds for the treatment and prevention of the above mentioned disorders, and for the manufacture of pharmaceutical compositions for the treatment and prevention of the above mentioned disorders.

The term "alkyl" as used herein denotes straight chain or branched alkyl residues containing 1 to 12 carbon atoms, such as methyl, ethyl, propyl, isopropyl, butyl, isobutyl, tert.-butyl, pentyl, amyl, 3-pentyl, hexyl, heptyl, octyl, nonyl, decyl, undecyl, dodecyl and the like.

The term "lower alkyl" as used herein denotes straight chain or branched alkyl residues containing 1 to 5 carbon atoms, such as methyl, ethyl, propyl, isopropyl, butyl, isobutyl, tert.-butyl, pentyl, amyl and 3-pentyl.

The term "perfluorinated lower alkyl" denotes alkyl groups as defined above wherein every hydrogen atom is substituted by fluorine, such as in trifluoromethyl, pentafluoroethyl, heptafluoropropyl and the like. Preferred perfluorinated lower alkyl groups are lower alkyl groups containing 1 to 3 carbon atoms, with 1 to 2 carbon atoms being especially preferred.

In the structural formulae presented herein a broken bond (...⫶⫶⫶) denotes that the substituent is below the plane of the paper and a wedged bond (⬤) denotes that the substituent is above the plane of the paper.

Preferred compounds of formula I are compounds wherein at least one of Y and Z is hydroxy, in especially preferred compounds Y and Z are hydroxy.

Especially preferred compounds of formula I are compounds wherein A is $—C\equiv C—$, for example (1R,3R)-5-[(2E,9Z)-12,12,12-trifluoro-11-hydroxy-7,7-dimethyl-11-trifluoromethyl-dodeca-2,9-dienylidene)-cyclohexane-1,3-diol;

(Z)-(1R,3S)-4-methylene-5-[(2E,9Z)-12,12,12-trifluoro-11-hydroxy-7,7-dimethyl-11-trifluoromethyl-dodeca-2,9-dienylidene]-cyclohexane-1,3-diol;

(Z)-(1R,3S)-5-((2E,9E)-12,12,12-trifluoro-11-trifluoromethyl-11-hydroxy-7,7-dimethyl-dodec-2,9-dienylidene)-4-methylene-cyclohexane-1,3-diol;

(1R,3R)-5-[(2E,9E)-12,12,12-trifluoro-11-trifluoromethyl-11-hydroxy-7,7-dimethyl-dodeca-2,9-dienylidene]-cyclohexane-1,3-diol;

(1R,3R)-5-[(2E,9E)-11-hydroxy-7,7,11-trimethyl-dodeca-2,9-dien-ylidene]-cyclohexane-1,3-diol;

(Z)-(S)-3-[(2E,9E)-11-hydroxy-7,7,11-trimethyl-dodeca-2,9-dien-ylidene]-4-methylene-cyclohexane-1-ol;

(1R,3R)-5-[(2E,9E)-12,12,12-trifluoro-11-trifluoromethyl-11-hydroxy-7,7-dimethyl-dodeca-2,9-dienylidene]-cyclohexane-1,3-diol.

Especially preferred are compounds of formula I wherein A represents a cis configurated double bond —CH═CH—.

A further preferred embodiment are compounds of formula I wherein A is —CH$_2$—CH$_2$—, for example (1R,3R)-5-[(2E)-12,12,12-trifluoro-11-hydroxy-7,7-dimethyl-11-trifluoromethyl-dodec-2-enylidene)-cyclohexane-1,3-diol;

(Z)-(1R,3S)-5-[(2E)-12,12,12-trifluoro-11-hydroxy-7,7-dimethyl-11-trifluoromethyl-dodec-2-enylidene]-4-methylene-cyclohexane-1,3-diol;

(Z)-(1S)-3-[(2E)-11-hydroxy-7,7,11-trimethyl-dodeca-2-en-ylidene]-4-methylene-cyclohexane-1-ol;

(Z)-(1R,3S)-5-[(E)-11-hydroxy-7,7,11-trimethyl-dodec-2-enylidene]-4-methylene-cyclohexane-1,3-diol;

(2E)-(1R,3R)-5-(11-hydroxy-7,7,11-trimethyl-dodeca-2-enylidene)-cyclohexane-1,3-diol.

Another preferred embodiment are compounds of formula I wherein A is —C≡C—, for example (E)-(1R,3R)-5-[12,12,12-trifluoro-11-hydroxy-7,7-dimethyl-11-trifluoromethyl-dodec-2-en-9-ynylidene]-cyclohexane-1,3-diol;

(Z)-(1R,3S)-4-methylene-5-[(E)-12,12,12-trifluoro-11-hydroxy-7,7-dimethyl-11-trifluoromethyl-dodec-2-en-9-ynylidene]-cyclohexane-1,3-diol;

(Z)-(S)-4-methylene-3-[(E)-12,12,12-trifluoro-11-hydroxy-7,7-dimethyl-11-trifluoromethyl-dodec-2-en-9-ynylidene]-cyclohexane-1-ol;

(10E,12Z)-(S)-12-(5-hydroxy-2-methylene-cyclohexylidene)-6,6-dimethyl-2-methyl-dodec-10-en-3-yn-2-ol;

(10E)-(3R,5R)-12-(3,5-dihydroxy-cyclohexylidene)-6,6-dimethyl-2-methyl-dodec-10-en-3-yn-2-ol.

The compounds of formula I can be obtained by cleavage of the silyl protecting groups contained in compounds of formula II

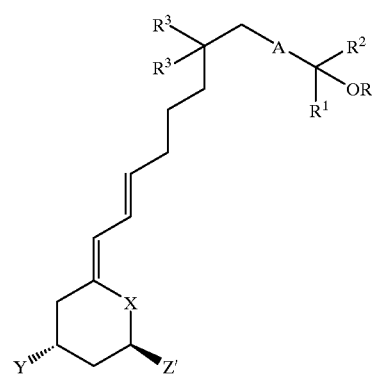

wherein Y' and Z' are protected hydroxy groups and R$^4$ is a hydroxy protecting group. Any conventional hydroxy protecting group can be utilized to protect the free hydroxy groups in the compounds of this invention. Any cleavable or hydrolyzable ether or ester group can be utilized. Preferred hydrolyzable ester groups are alkanoic esters and preferred hydrolyzable ether groups are silyl ethers such as tert-butyldimethyl-silyl (TBDMS) for the hydroxy groups Y and Z, whereas R$^4$ is preferably trimethyl-silyl [Si(CH$_3$)$_3$].

The cleavage of the hydroxy protection groups can be effected by any standard means such as where the silyl ethers are utilized cleavage can be effected by use of tetrabutylammonium fluoride (TBAF) in an inert solvent such as tetrahydrofuran. Mild acid hydrolysis can be used to cleave the alkanoic ester groups.

The intermediates II, which are novel and as such are a further object of the present invention can be prepared by a Wittig-reaction with a compound of formula III according to the reaction scheme 1 depicted below. Compounds of formula III may be prepared according to the method described in EP-A 0 771 789.

Scheme 1

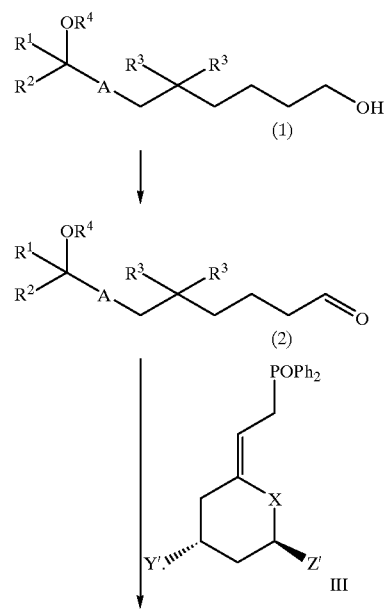

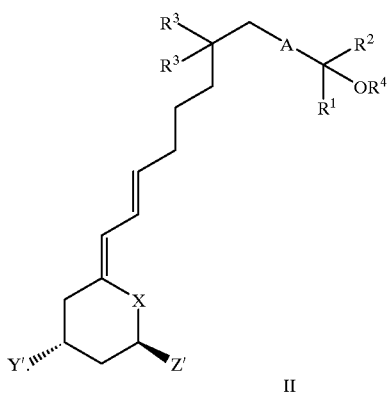

II wherein the symbols are as defined above.

Compounds of formula (1) which are oxidized to the aldehyde (2) can be prepared according to the reaction scheme 2:

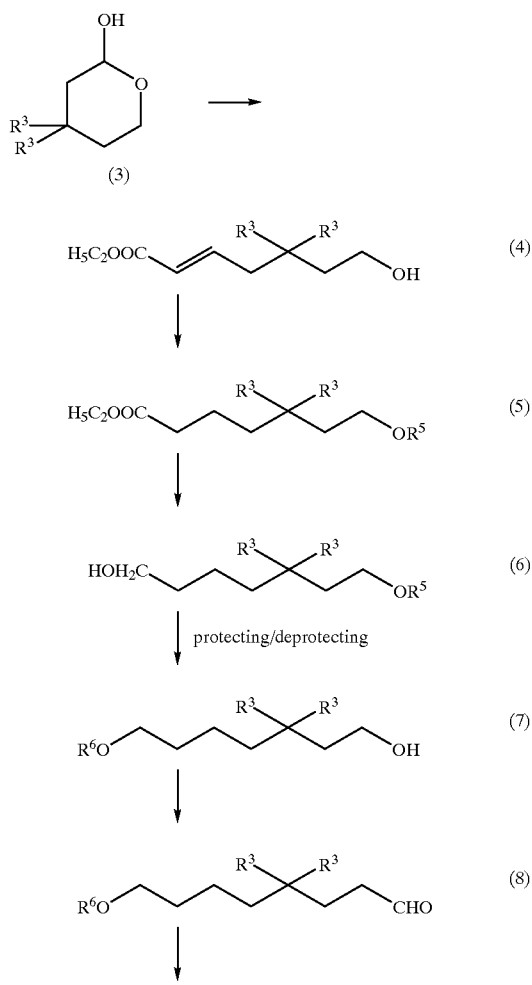

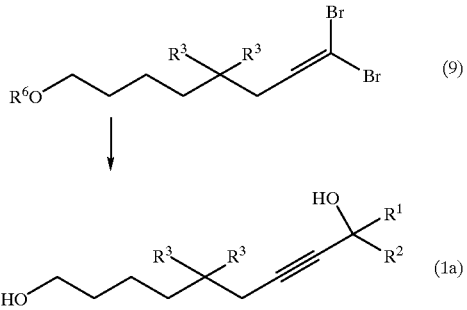

wherein $R^5$ represents a hydroxy protecting group, preferably the tert. butyldimethylsilyl group, $R^6$ respresents another hydroxy protecting group, preferably the tetrahydropyranyl group whereas $R^1$, $R^2$ and $R^3$ are as defined above.

Starting from known 4,4-dialkyl-tetrahydropyran-2-one the corresponding 4,4-alkyl-tetrahydropyran-2-ol (3) is obtained by reduction. The alcohol (3) is then reacted with ethoxycarbomethylene-triphosporane to form the corresponding 7-hydroxy-hepten-2-oic acid ester (4). After protection of the hydroxy group to yield the unsaturated ester (5) the double bond is catalytically hydrogenated before the ester group is reduced to form the corresponding mono protected diol (6). Protection and deprotection of the respective hydroxy groups yields the mono-protected diol (7) which is oxidized with a known oxidizing agent as for example 4-methyl-morpholine-4-oxide and tetrapropylammonium-perrhutenate to the aldehyde (8). This aldehyde is then first reacted with tetrabromomethane in the presence of 2 eqivalents of triphenylphosphine to form (9) and subsequently with butyllithium and the corresponding ketone derivative (eg. hexafluoroacetone for the preparation of compounds of formula I wherein $R^1$ and $R^2$ are trifluoromethyl) to yield, after final deprotection of the primary alcohol, compounds of formula (1a), i.e. compounds of formula (1) wherein A is —C≡C—. In order to obtain the corresponding compounds (1b), i.e. compounds wherein A represents —CH═CH—, and (1c), i.e. compounds wherein A represents —CH$_2$—CH$_2$—, further reduction steps are required.

Compounds of formula II may also be prepared by an alternate route as depicted in Scheme 3:

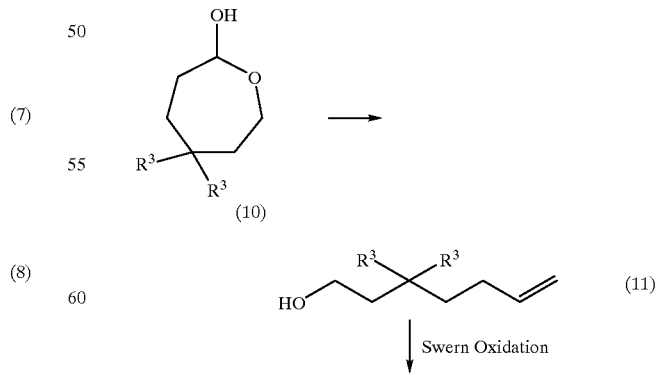

-continued

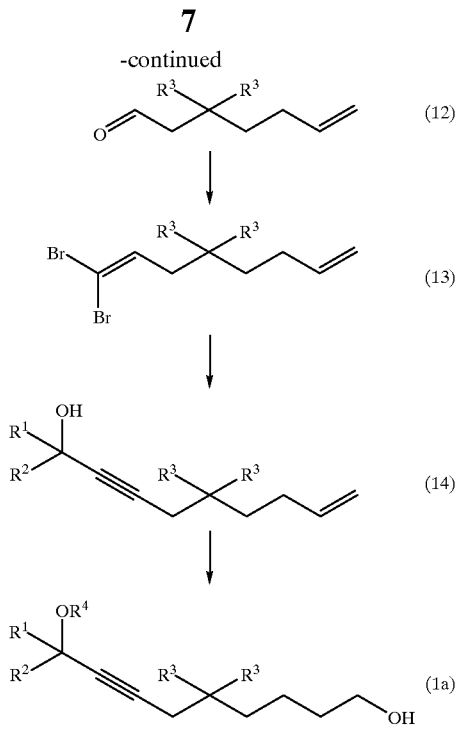

wherein the symbols are defined as above.

The pharmacological properties of the compounds of the formula I can be determined by the following test procedures:

1. Calcium Liability (Tolerance Test in Mice)

This test gives a global picture of calcemic liability. Profound changes in calcium homeostasis strongly affect the weight development of the animals. This parameter was used as a primary test for tolerance. Mice (25–30 g body weight) received daily subcutaneous administrations of the vitamin D derivative for 4 consecutive days. Body weight was registered just before and at the end of a 5 day treatment period. The "highest tolerated dose" ($HTD_{sc}$) in mice is the dose which results in zero weight gain during this treatment period.

The following compounds of formula I were tested:

A (1R,3R)-5-[(2E,9Z)-12,12,12-trifluoro-11-hydroxy-7,7-dimethyl-11-trifluoromethyl-dodeca-2,9-dienylidene)-cyclohexane-1,3-diol B (Z)-(1R,3S)-4-methylene-5-[(2E,9Z)-12,12,12-trifluoro-11-hydroxy-7,7-dimethyl-11-trifluoromethyl-dodeca-2,9-dienylidene]-cyclohexane-1,3-diol C (Z)-(1R,3S)-5-((2E,9E)-12,12,12-trifluoro-11-trifluoromethyl-11-hydroxy-7,7-dimethyl-dodec-2,9-dienylidene)-4-methylene-cyclohexane-1,3-diol D (1R,3R)-5-[(2E,9E)-12,12,12-trifluoro-11-trifluoromethyl-11-hydroxy-7,7-dimethyl-dodeca-2,9-dienylidene]-cyclohexane-1,3-diol E (1R,3R)-5-[(2E)-12,12,12-trifluoro-11-hydroxy-7,7-dimethyl-11-trifluoromethyl-dodec-2-enylidene)-cyclohexane-1,3-diol F (Z)-(1R,3S)-5-[(2E)-12,12,12-trifluoro-11-hydroxy-7,7-dimethyl-11-trifluoromethyl-dodec-2-enylidene]-4-methylene-cyclohexane-1,3-diol G (Z)-(1R,3S)-5-[(E)-11-hydroxy-7,7,11-trimethyl-dodec-2-enylidene]-4-methylene-cyclohexane-1,3-diol H (2E)-(1R,3R)-5-(11-hydroxy-7,7,11-trimethyl-dodeca-2-enylidene)-cyclohexane-1,3-diol I (E)-(1R,3R)-5-[12,12,12-trifluoro-11-hydroxy-7,7-dimethyl-11-trifluoromethyl-dodec-2-en-9-ynylidene]-cyclohexane-1,3-diol J (Z)-(1R,3S)-4-methylene-5-[(E)-12,12,12-trifluoro-11-hydroxy-7,7-dimethyl-11-trifluoromethyl-dodec-2-en-9-ynylidene]-cyclohexane-1,3-diol K (10E)-(3R,5R)-12-(3,5-dihydroxy-cyclohexylidene)-6,6-dimethyl-2-methyl-dodec-10-en-3-yn-2-ol The results are compiled in Table I below. For calcitriol a HTD of 0.5 µg/kg was observed. In comparison thereto, for the compounds of formula I (compounds A to K) HTD figures ranging from 80 to >5000 µg/kg were observed.

2. VDR Activation

In order to measure the activation of the vitamin D receptor (VDR) by vitamin D analogs in cells a transcription activation assay was used. COS cells were cotransfected with the human VDR (expressed in pSG5) and a reporter gene containing three response elements (VDRE3) from the rat osteocalcine gene, the thymidine kinase basal promoter, and the luciferase reporter gene, respectively.

From Table I it can be been that the listed compounds A to K are very potent with respect to VDR activation. Moreover all these compounds A to K have a greater therapeutic window than calcitriol (as indicated by the TI shift vs calcitriol).

TABLE I

| Compound | VDR act ($ED_{50}$, nanomolar) | HTDsc mouse µg/kg | HTD/VDR | TI shift |
|---|---|---|---|---|
| Calcitriol | 2.8 | 0.5 | 0.18 | 1 |
| A | 180 | 2500 | 14 | 78 |
| B | 50 | 3000 | 60 | 333 |
| C | 4 | 200 | 50 | 278 |
| D | 5.7 | 100 | 18 | 100 |
| E | 6.6 | 100 | 15 | 83 |
| F | 4 | 80 | 20 | 111 |
| G | 110 | >5000 | 45 | 250 |
| H | 280 | >5000 | 18 | 100 |
| I | 13 | 333 | 26 | 144 |
| J | 4.8 | 310 | 65 | 361 |
| K | 220 | >5000 | >23 | >127 |

HTDsc: highest tolerated subcutaneous dose (µg/kg) without weight loss
TI shift: shift in „therapeutic index", defined as the ratio HTD/VDR of the test compound divided by the ratio HTD/VDR of calcitriol.

3. The Mouse Model

Orally administered vitamin D analogues can lead to epidermal thickening (acanthosis) in hairless mice. This skin effect is considered as indicative for antipsoriatic potential of vitamin D analogues. Analogues were tested for 4 days at different dosages in order to detect compounds which show this epidermal effect at subtoxic and non-toxic doses (dosage leading to slight or no weight loss). At the higest tolerated dose calcitriol itself was not able to elicit skin effects. The calcitriol data were obtained from animals treated for three days.

Hairless mice (Moro hr/hr) received daily administrations of the test compound in arachis oil by gavage for 4 days, using 2–5 different dosages (3 fold increments; 2 animals per dosage group). Daily measurements of body weight allowed to judge toxicity (calcemic liability) and determine the non-toxic dose level defined as the dose which is tolerated without weight loss. The mice were sacrificed at day 5 and skin biopsies were taken, fixed in formalin and treated for histological evaluation.

The results in Table II below show that many of the retiferols of formula I, are far superior to calcitriol due to a better ratio between the effective dose and the maximal tolerated dose ($HTD_{po}$). This may translate in a better separation between wanted skin effects ($ED_{50}$) and toxic calcemic effects.

TABLE II

| Compound | $ED_{50}$ | HTDpo | ratio (TI) $HTD/ED_{50}$ | TI shift |
|---|---|---|---|---|
| calcitriol | 500 | 1 | 0.002 | 1 |
| A | 7500 | 1000 | 0.13 | 67 |
| B | 3000 | 400 | 0.13 | 67 |
| C | 450 | 60 | 0.13 | 67 |
| D | 500 | 50 | 0.1 | 50 |
| E | 200 | 40 | 0.2 | 100 |
| F | 200 | 80 | 0.4 | 200 |
| G | 60000 | 20000 | 0.33 | 167 |
| I | 800 | 100 | 0.125 | 63 |
| J | 700 | 70 | 0.1 | 50 |

$ED_{50}$: dose (µg/kg) causing half-maximal epidermal thickening
HTDpo$_o$ highest tolerated oral dose (µg/kg) without weight loss
TI shift: shift in „therapeutic index", is defined as ratio $HTD/ED_{50}$ for the test compound divided by the ratio $HTD/ED_{50}$ for calcitriol 4. The Pig Model Orally administered vitamin D analogs can lead to epidermal proliferation in minipigs. This skin effect is considered as indicative for an antipsoriatic potential of vitamin D analogs. Compounds were tested for seven days at different doses in order to detect those which showed a skin effect at non calcemic dose (no calcemic effect). The pigs were daily observed as to adverse effects such as behavior, mobility, stool. At day seven bromodeoxyuridine (4 mg/kg) was injected intravenously into the treated pigs and 2 hours later skin biopsies (6 mm diameter) and blood were taken for analysis. The skin biopsies were fixed in formalin, and paraffin sections were prepared using standard procedures. Using standard immuno-histochemical techniques, cells in the S-phase (DNA synthesis phase) were labelled by the binding of a specific monoclonal antibody against the thymidine analogue bromodeoxyuridine. The number of labelled epidermal cells per unit of length along the surface was taken as a measure of epidermal proliferative activity (labelings index LI). Clinical chemistry was performed using Cobas Mira. Calcitriol itself did not induce hyperproliferation even at highly toxic does (9 times the dose that induces hypercalcemia).

TABLE III

| Compound | Effective dose *µg/kg | Calcemic dose, µg/kg | TI (ratio Calc./Eff. | Rel. shift |
|---|---|---|---|---|
| calcitriol | >22.5 | 3 | <0.15 | 1 |
| A | 100 | 5000 | 50 | >350 |
| B | 1000 | 2000 | 2 | >14 |
| F | 3 | 15 | 5 | >35 |
| I | 36 | 200 | 6 | >42 |
| J | 108 | >324 | >3 | >>21 |

*The effective dose is the dose that increases the normal LI at least 50%

No adverse effects for compounds of formula I were noted at the effective dose.

The compounds of formula I can be administered orally, for the treatment or prevention of hyperproliferative skin diseases such as psoriasis, basal cell carcinomas, disorders of keratinization, and keratosis, or for the treatment of neoplastic diseases, to warmblooded animals which need such treatment. More specifically, the compounds according to the invention as described above can be administered orally to an adult human in dosages that are in the range of about 50 µg to 500 mg per day for the treatment of the above diseases.

The compounds of formula I can be administered topically, for the treatment or prevention of hyperproliferative skin diseases such as psoriasis, to warmblooded animals which need such treatment. More specifically, these compounds can be administered topically in dosages that are in the range of about 50 µg to 500 mg per gram of topical formulation per day, for the treatment of the above diseases.

The compounds of formula I can also be administered orally or topically for reversing the conditions associated with photodamage.

The dosage of the compounds of formula I can vary within wide limits depending on the illness to be treated, the age and the individual condition of the patient and on the mode of administration and will, of course, be fitted to the individual requirements in each particular case.

Oral dosage forms comprising compounds of formula I, may be incorporated in capsules, tablets and the like with pharmaceutically acceptable carrier materials. Illustrative of such carrier materials which may be incorporated into capsules, and the like are the following: an emulsifier such as polyethylene glycol; a solubilizer such as a short chain triglyceride, e.g. Miglyol; a binder such as gum tragacanth, acacia, corn starch, or gelatin; an excipient such as dicalcium phosphate; a disintegrating agent such as corn starch, potato starch or algenic acid; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the disorder for the exertion of local action. Accordingly, the topical composition include those pharmaceutical forms in which compounds of formula I are applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following pharmaceutical compositions can be prepared in a manner known per se:

EXAMPLE A

| Soft Gelatine Capsule | | mg/Capsule |
|---|---|---|
| Active Compound | | 50 |
| Butylated Hydroxytoluene (BHT) | | 0.016 |
| Butylated Hydroxyanisole (BHA) | | 0.016 |
| Fractionated Coconut Oil (Neobee M-5) or Miglyol 812 | q.s. | 160.0 |

EXAMPLE B

| Soft Gelatine Capsule | | mg/Capsule |
|---|---|---|
| Active Compound | | 50 |
| α-Tocopherol | | 0.016 |
| Miglyol 812 | q.s. | 160.0 |

EXAMPLE C

| Topical Cream | mg/g |
|---|---|
| Active Compound | 20 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. |

EXAMPLE D

| Topical ointment | mg/g |
|---|---|
| Active Compound | 20 |
| Propylenglycol | exc. ad ung. pro 1 g |

EXAMPLE 1

A: Preparation of (1R,3R)-5-[(2E,9Z)-12,12,12-Trifluoro-11-hydroxy-7,7-dimethyl-11-trifluoromethyl-dodeca-2,9-dienylidene)-cyclohexane-1,3-diol a] 4,4-Dimethyl-tetrahydro-pyran-2-ol 6.05 g of 4,4-Dimethyl-tetrahydro-pyran-2-one (47.2 mmol) was dissolved in 125 ml of abs. tetrahydrofuran and cooled down to −78°. 53.1 ml of diisobutylaluminumhydride (1.2M, toluene) was slowly added while keeping the temperature below −72°. After 90 Min., GC-analysis indicated 97% of product. The excess of reagent was destroyed by adding at −78° 1.18 ml of methanol, followed by 76 ml of 2N HCl. Twofold extraction with ether, washing with NaCl, drying over sodium sulfate and evaporation of the solvents left a crude product which was purified by flash chromatography ($SiO_2$, pentane/methylacetate=7/3) to yield 5.57 g of the title compound as colorless oil, 99% pure according to GC.

b] 7-Hydroxy-5,5-dimethyl-hept-2-enoic acid ethyl ester 5.57 g of 4,4-Dimethyl-tetrahydro-pyran-2-ol (42.8 mmol) and 26.3 g of ethoxycarbonylmethylentriphenylphosphorane (1.76 eq.) was heated together under Argon in 277 ml of $CH_3CN$ for 24 h at 90°. The volume was reduced to about 50 ml, the remaining solution was then poured onto crushed ice/$NH_4Cl$, extracted twice with ether, dried over sodium sulfate, and the solvents removed. Flash chromatography ($SiO_2$, hexane/ethylacetate=7/3) produced 7.42 g of the title compound as yellowish oil (E/Z ca. 86/14).

NMR: (main isomer, 1H, δ, TMS) 0.96 (s, 6H), 1.29 (t, 3H), 1.55 (t, 2H), 2.13 (dd, 2H), 3.72 (t, 2H), 4.19 (q, 2H), 5.82 (dt, 1H), 6.98 (dt, 1H), 1.6 (br, OH).

c] 7-(tert-Butyl-dimethyl-silanyloxy)-5,5-dimethyl-hept-2-enoic acid ethyl ester 7.42 g of 7-Hydroxy-5,5-dimethyl-hept-2-enoic acid ethyl ester (37.05 mmol) was dissolved in 18 ml of abs. N,N-dimethylformamide and treated at 0° with 7.56 g of imidazole (3 eq.) and 8.38 g of tert-butyl-dimethyl-chlorosilane (1.5 eq.). The reaction mixture was kept at room temperature over night and then poured onto crushed ice, extracted twice with ether, washed with water, dried over sodium sulfate and evaporated to dryness. Flash chromatography ($SiO_2$, hexane/ethylacetate=97/3) yielded 9.94 g of the title compound as colourless oil, again as E/Z-mixture.

d] 7-(tert-Butyl-dimethyl-silanyloxy)-5,5-dimethyl-heptanoic acid ethyl ester 9.94 g of 7-(tert-Butyl-dimethyl-silanyloxy)-5,5-dimethyl-hept-2-enoic acid ethyl ester (31.6 mmol), dissolved in 315 ml of ethylacetate, was hydrogenated over 2.6 g of Pd/C (5%) at room temperature and atmospheric pressure during 100 Min. The reaction mixture was filtered over a pad of Celite and the solvents removed to leave 9.95 g of the title compound, 97.5% pure according to GC.

NMR: (1H, δ, TMS) 0.04 (s, 6H), 0.87 (s, 6H), 0.88 (s, 9H), 1.20 (m, 2H), 1.25 (t,3H), 1.46 (t, 2H), 1.55 (m, 2H), 2.25 (t, 2H), 3.64 (t, 2H), 4.12 (q, 2H).

e] 7-(tert-Butyl-dimethyl-silanyloxy)-5,5-dimethyl-heptan-1-ol 9.95 g of 7-(tert-Butyl-dimethyl-silanyloxy)-5,5-dimethyl-heptanoic acid ethyl ester (31.4 mmol) was dissolved in 125 ml of abs. tetrahydrofuran and cooled down to −10°. 65.5 ml of diisobutylaluminumhydride (1.2M, toluene) was slowly added while keeping the temperature below 0°. After 25 Min. the reaction mixture was quenched with water, extracted twice with ether, both layers were filtered over a pad of Celite (to remove Al-salts), the ethereal solution washed with water, dried over sodium sulfate and evaporated to dryness. Flash chromatography ($SiO_2$, hexane/ethylacetate=8/2) produced 8.23 g of the title compound as slightly yellow oil, >99% pure according to GC.

NMR: (1H, δ, TMS) 0.05 (s, 6H), 0.87 (s, 6H), 0.89 (s, 9H), 1.15–1.6 (m, 8H+OH), 3.65 (2×t, 2×2H).

f] tert-Butyl-[3,3-dimethyl-7-(tetrahydro-pyran-2-yloxy)-heptyloxy]-dimethyl-silane 8.23 g of 7-(tert-Butyl-dimethyl-silanyloxy)-5,5-dimethyl-heptan-1-ol (30.0 mmol) was dissolved in 58 ml of $CH_2Cl_2$ and treated with 4.75 ml of 3,4-dihydro-2H-pyrane (1.75 eq.) and 751 mg of pyridinium-(toluene-4-sulfonate) (0.1 eq.). After 60 h at ambient temberature, the reaction mixture was poured onto crushed ice/$Na_2CO_3$, extracted twice with ether, washed with brine, dried over sodium sulfate and evaporated to dryness. Flash chromatography ($SiO_2$, hexane/ethylacetate=97/3) yielded 10.17 g of the title compound as colourless oil.

NMR: (1H, δ, TMS) 0.05 (s, 6H), 0.87 (s, 6H), 0.89 (s, 9H), 1.15–1.9 (m, 14H), 3.37 (dt, 1H), 3.50 (m, 1H), 3.64 (t, 2H), 3.75 (dt, 1H), 3.88 (m, 1H), 4.58 (m, 1H).

g] 3,3-Dimethyl-7-(tetrahydro-pyran-2-yloxy)-heptan-1-ol 10.17 g of tert-Butyl-[3,3-dimethyl-7-(tetrahydro-pyran-2-yloxy)-heptyloxy]-dimethyl-silane (28.4 mmol) was treated with 3 eq. of dry tetrabutylammoniumfluoride trihydrate (0.3M in tetrahydrofurane). After 90 Min. at room temperature, the mixture was poured onto crushed ice/ether. Usual workup followed by flash chromatography ($SiO_2$, hexane/ethylacetate=7/3) gave 6.28 g of the title compound as colourless oil.

h] 3,3-Dimethyl-7-(tetrahydro-pyran-2-yloxy)-heptanal 8.30 g of 4-Methyl-morpholin-4-oxide.$H_2O$ (61 mmol) and 574 mg of tetrapropylammoniumperrhutenate (1.63 mmol) in 160 ml of $CH_2Cl_2$ was dried by stirring for 2 h at room temperature over 46 g of molecular sieves (4 Å pulv.). 4.00 g of 3,3-Dimethyl-7-(tetrahydropyran-2-yloxy)-heptan-1-ol, dissolved in 80 ml of $CH_2Cl_2$, was then added within 90 Min. Filtration over a pad of Celite, removal of the solvent and flash chromatography ($SiO_2$, hexane/ethylacetate=9/1) delivered 2.82 g of the title compound as colourless oil, 99% pure according to GC.

NMR: (1H, δ, TMS) 1.05 (s, 6H), 1.3–1.95 (m, 12H), 2.26 (d, 2H), 3.39 (dt, 1H), 3.50 (m, 1H), 3.75 (dt, 1H), 3.87 (m, 1H), 4.58 (m, 1H), 9.84 (t, 1H).

i] 2-(8,8-Dibromo-5,5-dimethyl-oct-7-enyloxy)-tetrahydropyran 7.48 g of $CBr_4$ (22.6 mmol) in 113 ml of $CH_2Cl_2$ was reacted at −18° with 11.83 g (45.1 mmol) of triphenylphosphine. After 5 Min., 2.82 g of 3,3-dimethyl-7-(tetrahydro-pyran-2-yloxy)-heptanal, dissolved in 21 ml of $CH_2Cl_2$, was added dropwise. 45 Min. later, the reaction mixture was diluted with hexane, washed twice with ethanol/$H_2O$=8/2 to remove the triphenylphosphine oxide, the hexane layer was dried over sodium sulfate and evaporated to dryness. Flash chromatography ($SiO_2$, hexane/ethylacetate=9/1) afforded 4.554 g of the title compound as colourless oil.

NMR: (1H, δ, TMS) 0.90 (s, 6H), 1.2–1.9 (m, 12H), 2.01 (d, 2H), 3.39 (dt, 1H), 3.49 (m, 1H), 3.75 (dt, 1H), 3.87 (m, 1H), 4.58 (m, 1H), 6.41 (t, 1H).

j] 1,1,1-Trifluoro-2-trifluoromethyl-6,6-dimethyl-10-(tetrahydro-pyran-2-yloxy)-dec-3-yn-2-ol 4.554 g of 2-(8,8-Dibromo-5,5-dimethyl-oct-7-enyloxy)-tetrahydro-pyrane (11.44 mmol) was dissolved in 50 ml of abs. tetrahydrofuran and treated at −78° with 22.14 ml of n-butyllithium (1.55 M, hexane, 3 eq.). 30 Min. later, a large excess of hexafluoro-acetone was introduced into the reaction flask and allowed to react for ½ h. Pouring onto crushed ice, twofold extraction with ether, washing with brine, drying over sodium sulfate and evaporation of the solvents left a crude product which was purified by flash chromatography ($SiO_2$, hexane/ethylacetate=85/15) to yield 5.60 g of the title compound as colorless oil.

k] 10,10,10-Trifluoro-9-trifluoromethyl-5,5-dimethyl-dec-7-yne-1,9-diol 3.00 g of 1,1,1-Trifluoro-2-trifluoromethyl-6,6-dimethyl-10-(tetrahydro-pyran-2-yloxy)-dec-3-yn-2-ol (6.1 mmol) was dissolved in 40 ml of methanol, treated with 231 mg of pyridinium(toluene-4-sulfonate) (0.919 mmol), and kept at room temperature over night. The reaction mixture was then poured onto crushed ice/$Na_2CO_3$, extracted twice with ether, washed with brine, dried over sodium sulfate and evaporated to dryness. Flash chromatography ($SiO_2$, hexane/ethylacetate=7/3) gave 1.736 g of the title compound as yellowish oil.

l] (Z)-10,10,10-Trifluoro-9-trifluoromethyl-5,5-dimethyl-dec-7-ene-1,9-diol 588 mg of 10,10,10-Trifluoro-9-trifluoromethyl-5,5-dimethyl-dec-7-yne-1,9-diol (1.84 mmol) in 10 ml of ethylacetate was hydrogenated over 100 mg of Pd/C (10%) at room temperature and atmospheric pressure during 100 Min. The reaction mixture was filtered over a pad of Celite and the solvents removed to leave 559 mg of the title compound, used as such for the next step.

NMR: (1H, δ, TMS) 0.93 (s, 6H), 1.2–1.4 (m, 6H+1OH), 2.39 (d, 2H), 3.67 (t, 2H), 4.15 (br s, 1OH), 5.52 (br d, 1H), 6.09 (dt, 1H).

CI-MS: $(M+NH_4)^+$ 340.

m] (Z)-10,10,10-Trifluoro-9-trifluoromethyl-9-hydroxy-5,5-dimethyl-dec-7-enal 555 mg of (Z)-10,10,10-Trifluoro-9-trifluoromethyl-5,5-dimethyl-dec-7-ene-1,9-diol (1.722 mmol) was oxidized by reaction with 2.45 g of pyridinium-dichromate (3.8 eq.) in 54 ml of $CH_2Cl_2$ at room temperature over night. Filtration over a pad of Celite, removal of the solvent and flash chromatography ($SiO_2$, pentane/AcOMe=8/2) furnished 425 mg of the title compound as colourless oil.

NMR: (1H, δ, TMS) 0.93 (s, 6H), 1.20 (m, 2H), 1.60 (m, 2H), 2.42 (br d, 2H), 2.44(t, 2H), 3.71 (s, OH), 5.53 (br d, 1H), 6.09 (dt, 1H), 9.76 (s, 1H).

MS: $(M)^+$ 320, $(M−CH_3−H_2O)^+$ 287.

n] (Z)-10,10,10-Trifluoro-9-trifluoromethyl-5,5-dimethyl-9-trimethylsilanyloxy-dec-7-enal 1.860 g of (Z)-10,10,10-Trifluoro-9-trifluoromethyl-9-hydroxy-5,5-dimethyl-dec-7-enal (5.80 mmol) was dissolved in 20 ml of $CH_2Cl_2$ and treated successively at 0° with 71 mg of dimethylaminopyridine (0.1 eq.), 4.74 g of triethylamine (8 eq.), and 3.81 g of $(CH_3)_3SiCl$ (6 eq.). After stirring for 40 Min. at room temperature, the reaction mixture was poured onto crushed ice/hexane, the organic layer washed with water, dried over sodium sulfate and evaporated to dryness. Flash chromatography ($SiO_2$, pentane/methylacetate=96/4) yielded 1.495 g of the title compound as colourless oil.

NMR: (1H, δ, TMS) 0.23 (s, 9H), 0.91 (s, 6H), 1.24 (m, 2H), 1.60 (m, 2H), 2.38 (br d, 2H), 2.42(t, 2H), 5.46 (br d, 1H), 5.97 (dt, 1H), 9.77 (s, 1H).

o] (1R,3R)-1,3-Bis-(tert-butyl-dimethyl-silanyloxy)-5-((2E,9Z)-12,12,12-trifluoro-7,7-dimethyl-11-trifluoromethyl-11-trimethylsilanyloxy-dodeca-2,9-dienylidene)-cyclohexane 2.20 g of carefully dried (3R,5R)-[2-[3,5-bis-(t-butyldimethyl-silanyloxy)-cyclohexylidene]-ethyl]-diphenyl-phosphine oxide (*Tetrahedron Lett.* 32, 7663 (1991)) (1.4 eq.) was dissolved in 25 ml of abs. tetrahydrofuran and treated at −78° with 2.48 ml of n-butyllithium (1.55M, hexane). After 10 Min., 1.080 g of (Z)-10,10,10-trifluoro-9-trifluoromethyl-5,5-dimethyl-9-trimethylsilanyloxy-dec-7-enal, dissolved in 10 ml of abs. tetrahydrofurane, was added dropwise to the deep red solution. The mixture was kept for 0.75 h at −78° and then quenched with $NH_4Cl$ solution. Extraction with ethylacetate, washing with water, drying over sodium sulfate and evaporation of the solvents left a crude product which was purified by short flash chromatography ($SiO_2$, hexane/ethyl acetate=7/3) to yield 2.35 g of diastereomeric β-hydroxy-phosphine oxides which were processed as follows:

This intermediate was dissolved in 20 ml of abs. tetrahydrofuran and treated at −15° with roughly 4 eq. of NaH (50% in mineral oil). The temperature was slowly raised to room temperature and stirring continued, until thin layer chromatography indicated the absence of starting material (3 h). After quenching with crushed ice/$NH_4Cl$, the product was extracted with hexane, washed with water, dried over sodium sulfate and the solvents removed. Flash chromatography (SiO$_2$, hexane/ethylacetate=96/4) afforded 1.08 g of the title compound as colourless oil.

p] (1R,3R)-5-[(2E,9Z)-12,12,12-Trifluoro-11-hydroxy-7,7-dimethyl-11-trifluoromethyl-dodeca-2,9-dienylidene)-cyclohexane-1,3-diol 4.56 g of tetrabutylammoniumfluoride trihydrate (14.4 mmol) in 20 ml of tetrahydrofuran was carefully dried by stirring during 2 h at room temperature over 5 g of 3 Å molecular sieve. This solution was then added to the above prepared 1.08 g of (1R,3R)-1,3-bis-(tert-butyl-dimethylsilanyloxy)-5-((2E,9Z)-12,12,12-trifluoro-7,7-dimethyl-11-trifluoromethyl-11-trimethylsilanyloxy-dodeca-2,9-dienylidene)-cyclohexane (1.60 mmol) and kept for 2 h at 40°. The reaction mixture was then poured onto crushed ice/NH$_4$Cl, extracted twice with ethylacetate, washed with water, dried over sodium sulfate and evaporated to dryness. Flash chromatography (SiO$_2$, hexane/ethylacetate=35/65) yielded 699 mg of the title compound as colourless varnish. Typically, this product is contaminated with small amounts of 2Z-isomer which can be removed and isolated by HPLC (Microsorb Si 80-120-C5 from RAININ, solvent: hexane/iso-propanol 9/1).

MS: (M)$^+$ 444, (M–H$_2$O)$^+$ 426.

IR (cm$^{-1}$): 3350, 2940, 1665, 1304, 1265, 1217, 1172, 1147, 966.

NMR: (1H, δ, TMS) 0.89 (s, 6H), 1.2–1.5 (m, 4H), 1.60 (br s, 2H, OH), 1.88 (t, 2H), 2.0–2.7 (m, 8H), 3.94 (br s, 1H, OH), 4.10 m, 2H), 5.46 (br d, 1H), 5.69 (dt, 1H), 5.97–6.13 (m, 2H), 6.26 (m, 1H).

B. Alternate Method for the Preparation of (1R,3R)-5-[(2E,9Z)-12,12,12-Trifluoro-11-hydroxy-7,7-dimethyl-11-trifluoromethyl-dodeca-2,9-dienylidene)-cyclohexane-1,3-diol a] 5,5-Dimethyl-oxepan-2-ol 15.12 g of 5,5-Dimethyl-oxepan-2-one (106.3 mmol) was dissolved in 500 ml of abs. tetrahydrofuran and cooled down to –78°. 173 ml of diisobutylaluminumhydride (1.0M, hexane) was slowly added via dropping funnel while keeping the temperature below –70°. After 90 Min. at –78°, the excess of reagent was destroyed by adding 4 ml of methanol, followed by quenching with ice/NH$_4$Cl-solution. Twofold extraction with ether, washing with HCl and NaHCO$_3$, drying over sodium sulfate and evaporation of the solvents left a crude product which was used as such for the next step. According to $^1$H NMR it exists as mixture of lactol and hydroxy-aldehyde.

b] 3,3-Dimethyl-hept-6-en-1-ol 12.24 g of 5,5-Dimethyl-oxepan-2-ol (84.8 mmol) was dissolved in 375 ml of abs. tetrahydrofurane. 75.81 g of Methyltriphenylphosphonium bromide (2.5 eq.) was added and the reaction vessel cooled down to –16°. 23.81 g of potassium tert.butylate (2.5 eq.) was added in one portion (slightly exothermic) and the reaction mixture stirred at room temperature for 4.5 g. Pouring onto crushed ice/NH$_4$Cl-solution, twofold extraction with ether, washing with brine, drying over sodium sulfate and evaporation of the solvents left a crude product which was purified by flash chromatography (SiO$_2$, hexane/ethylacetate=8/2) to yield 9.95 g of the title compound as yellowish oil.

MS: (M–H$_2$O—CH$_3$)$^+$ 109.

NMR: (1H, δ, TMS) 0.85 (s, 6H), 1.23 (m, 2H), 1.38 (t, 2H), 1.99 (m, 2H), 3.42 (m, 2H), 4.22 (t, OH), 4.87 (br d, 1H), 5.00 (br d, 1H), 5.82 (m, 1H).

c] 3,3-Dimethyl-hept-6-enal

Swern reagent was prepared at –65° C. by adding slowly 11.95 ml (168 mmol) of abs. dimethylsulfoxide, dissolved in 45 ml of abs. CH$_2$Cl$_2$, to a solution of 6.60 ml (76.8 mmol) of oxalyl chloride in 200 ml of CH$_2$Cl$_2$ (exothermic!). After 30 Min., 9.95 g of 3,3-dimethyl-hept-6-en-1-ol (69.9 mmol), dissolved in 70 ml of CH$_2$Cl$_2$, was slowly added (strongly exothermic!). After 1 h at –60° C., 33.0 ml (237 mmol) of triethylamine was added dropwise and the temperature allowed to reach 0° C. The reaction was quenched by pouring onto crushed ice/HCl, extracted twice with CH$_2$Cl$_2$, washed with Na$_2$CO$_3$-solution, dried over sodium sulfate and the volume reduced to about 100 ml. Due to its high volatility, this product was directly processed as follows.

d] 1,1-Dibromo-4,4-dimethyl-octa-1,7-diene 34.80 g (104.9 mmol) of CBr$_4$ in 285 ml of abs. CH$_2$Cl$_2$ was treated with 55.04 g (209.8 mmol) of triphenylphosphine at –15° C. After 10 Min., the above prepared aldehyde solution (<69 mmol) was added dropwise and the mixture kept for 15 Min. at –10° C. The reaction mixture was then partitioned twice between hexane and ethanol/water=8/2, the upper layer washed with ethanol/water=8/2, dried over sodium sulfate, and the solvents removed. Flash chromatography (SiO$_2$, hexane) delivered 16.31 g of the title compound as colorless oil.

MS: (M–C$_4$H$_7$)$^+$ 241.

NMR: (1H, δ, TMS) 0.92 (s, 6H), 1.31 (m, 2H), 2.02 (m, 4H), 4.94 (br d, 1H), 5.02 (br d, 1H), 5.82 (m, 1H), 6.42 (t, 1H).

e] 1,1,1-Trifluoro-2-trifluoromethyl-6,6-dimethyl-dec-9-en-3-yn-2-ol 16.31 g of 1,1-Dibromo-4,4-dimethyl-octa-1,7-diene (55.09 mmol) was dissolved in 240 ml of abs. tetrahydrofuran and treated at –74° with 107 ml of n-butyllithium (1.55 M, hexane, 3 eq.). 30 Min. later, a large excess of hexafluoro-acetone (ca. 38 g) was introduced into the reaction flask and allowed to react for ½ h. The temperature was rised to –10° C. and the reaction quenched by pouring onto crushed ice. Twofold extraction with ether, washing with NH$_4$Cl, drying over sodium sulfate and evaporation of the solvents left a crude product which was purified by flash chromatography (SiO$_2$, hexane/ethylacetate=9/1) to yield 20.18 g of the title compound as colorless oil.

MS: (M–CH$_3$)$^+$ 287.

NMR: (1H, δ, TMS) 0.99 (s, 6H), 1.38 (m, 2H), 2.02 (m, 2H), 2.19 (s, 2H), 3.19 (s, OH), 4.95 (br d, 1H), 5.02 (br d, 1H), 5.81 (m, 1H).

f] 10,10,10-Trifluoro-9-trifluoromethyl-5,5-dimethyl-dec-7-ene-1,9-diol 18.6 mmol of a thexyl-borane-solution (0.5M, tetrahydrofurane) was prepared according to standard procedure (*J. Am. Chem. Soc.* 94, 3567 (1972)). 6.50 g of 1,1,1-Trifluoro-2-trifluoromethyl-6,6-dimethyl-dec-9-en-3-yn-2-ol (16.9 mmol), dissolved in 37 ml of tetrahydrofurane, was added dropwise at 0° C. and allowed to react for 10 Min. at 0° C. and for 0.5 h at room temperature. 14.8 g of H$_2$O$_2$ (35%) and 19.3 g of NaOH (28%) was added carefully (strongly exothermic!) and the mixture vigorously stirred for 30 Min. at 35–40°. The reaction mixture was then poured onto crushed ice/NH$_4$Cl-solution, extracted twice with ether, washed with hydrogensulfite-solution and brine, dried over sodium sulfate, and evaporated to dryness. Flash chromatography (SiO$_2$, hexane/ethylacetate=7/3) afforded 4.09 g of the title compound as colorless oil.

g] (Z)-10,10,10-Trifluoro-9-trifluoromethyl-5,5-dimethyl-dec-7-ene-1,9-diol 4.09 g of 10,10,10-Trifluoro-9-trifluoromethyl-5,5-dimethyl-dec-7-ene-1,9-diol (12.77 mmol) was dissolved in 80 ml of ethylacetate and hydrogenated over 0.80 g of Pd/C (10%) at room temperature and atmospheric pressure during 110 Min. The reaction mixture was filtered over a pad of Celite and the solvents removed. Flash chromatography ($SiO_2$, hexane/ethylacetate=8/2) produced 3.10 g of the title compound as colorless oil, identical to the product obtained in example 1/step 1].

EXAMPLE 2

Preparation of (Z)-(1R,3S)-4-Methylene-5-[(2E,9Z)-12,12,12-trifluoro-11-hydroxy-7,7-dimethyl-11-trifluoromethyl-dodeca-2,9-dienylidene]-cyclohexane-1,3-diol In analogy to example 1, but using in step o] (Z)-(3S, 5R)-[2-[3,5-bis-(t-butyldimethylsilanyloxy)-2-methylene-cyclohexylidene]-ethyl]-diphenyl-phosphine oxide, respectively, was prepared:
(Z)-(1R,3S)-4-Methylene-5-1(2E,9Z)-12,12,12-trifluoro-11-hydroxy-7,7-dimethyl-11-trifluoromethyl-dodeca-2,9-dienylidene]-cyclohexane-1,3-diol as colourless oil.

MS: $(M)^+$ 456, $(M-H_2O)^+$ 438.

IR ($cm^{-1}$): 3340, 2940, 1308, 1264, 1211, 1170, 1145, 964.

NMR: (1H, δ, TMS) 0.88 (s, 6H), 1.15–1.6 (m, 4H), 1.60 (br s, 2H, OH),k 1.97 (t, 2H), 2.0–2.65 (m, 6H), 3.75 (br s, 1H, OH), 4.24 m, 1H), 4.44 (br t, 1H), 5.00 (brs, 1H), 5.32 (br s, 1H), 5.45 (br d, 1H), 5.70 (dt, 1H), 6.00–6.14 (m, 2H), 6.39 (m, 1H).

EXAMPLE 3

Preparation of (Z)-(1R,3S)-5-((2E,9E)-12,12,12-Trifluoro-11-trifluoromethyl-11-hydroxy-7,7-dimethyl-dodec-2,9-dienylidene)-4-methylene-cyclohexane-1,3-diol a] (E)-1,1,1-Trifluoro-2-trifluoromethyl-6,6-dimethyl-10-(tetrahydro-pyran-2-yloxy)-dec-3-en-2-ol 191 mg of $LiAlH_4$ (5 eq.) was suspended in 18 ml of abs. tetrahydrofuran and cooled down to 0°. 271 mg of sodium methylate (5 eq.) was added, followed by a solution of 408 mg of 1,1,1-trifluoro-2-trifluoromethyl-6,6-dimethyl-10-(tetrahydro-pyran-2-yloxy)-dec-3-yn-2-ol (1.01 mmol) (example 1step j]), dissolved in 11 ml of tetrahydrofurane. The mixture was heated to reflux for 2 h and then, at 0°, carefully quenched with 1.6 ml of water and 1.6 ml of 2N NaOH. 27 ml of ether was then added and the mixture vigorously stirred to complete hydrolysis of the Al-salts. Drying over magnesium sulfate and evaporation of the solvents left 334 mg of the title product as colourless oil, sufficiently pure for the next step.

MS: $(M-H)^+$ 405.

b] (E)-10,10,10-Trifluoro-9-trifluoromethyl-5,5-dimethyl-dec-7-ene-1,9-diol 334 mg of (E)-1,1,1-Trifluoro-2-trifluoromethyl-6,6-dimethyl-10-(tetrahydro-pyran-2-yloxy)-dec-3-ene-2-ol (0.821 mmol) was dissolved in 6 ml of methanol, treated with 21 mg of pyridinium-(toluene-4-sulfonate) (0.1 eq.) and kept at room temperature for 24 h. The reaction mixture was then poured onto crushed ice/$Na_2CO_3$, extracted twice with ether, washed with brine, dried over sodium sulfate and evaporated to dryness. Flash chromatography ($SiO_2$, hexane/ethylacetate=7/3) afforded 224 mg of the title compound as colourless oil.

MS: $(M-CH_3-H_2O)^+$ 289.

NMR: (1H, δ, TMS) 0.90 (s, 6H), 1.2–1.6 (m, 6H+2OH), 2.06 (br d, 2H), 3.67 (t, 2H), 4.15 (br s, 1OH), 5.57 (d, 1H, J=16), 6.32 (dt, 1H, J=16, J=8).

c] (E)-10,10,10-Trifluoro-9-trifluoromethyl-9-hydroxy-5,5-dimethyl-dec-7-enal 417 mg of (E)-10,10,10-Trifluoro-9-trifluoromethyl-5,5-dimethyl-dec-7-ene-1,9-diol (1.294 mmol) was oxidized by reaction with 1.84 g of pyridinium-dichromate (3.8 eq.) in 40 ml of $CH_2Cl_2$ at room temperature over night. Filtration over a pad of silica gel, removal of the solvent and flash chromatography ($SiO_2$,hexane/ethylacetate=8/2) furnished 333 mg of the title compound as colourless oil.

MS: $(M-CH_3-H_2O)^+$ 289.

d] (3E,10E)-12-[(Z)-(3S,5R)-3,5-Bis-(tert-butyl-dimethyl-silanyloxy)-2-methylene-cyclohexylidene]-1,1,1-trifluoro-6,6-dimethyl-2-trifluoromethyl-dodeca-3,10-dien-2-ol 1.515 g of carefully dried (Z)-(3S,5R)-[2-[3,5-bis-(t-butyldimethyl-silanyloxy)-2-methylene-cyclohexylidene]-ethyl]-diphenyl-phosphine oxide (2.5 eq.) was dissolved in 9 ml of abs. tetrahydrofuran and treated at –78° with 1.96 ml of n-butyllithium (1.5 M, hexane). 20 Minutes later, 333 mg of (E)-10,10,10-tri fluoro-9-tri fluoromethyl-9-hydroxy-5,5-dimethyl-dec-7-enal (1.04 mmol), dissolved in 4 ml tetrahydrofurane, was added to the deep red solution, kept for 1 h at –78° and then quenched with $NH_4Cl$ solution. Extraction with ether, washing with water, drying over sodium sulfate and evaporation of the solvents left a crude product which was purified by flash chromatography ($SiO_2$, hexane/ethylacetate=7/3, then ethylacetate) to yield, besides the excess of starting phosphine oxide in the more polar fractions, 857 mg of diastereomeric β-hydroxy-phosphine oxides which were processed as follows:

This intermediate was dissolved in 8 ml of abs. tetrahydrofuran and treated at 0° with roughly 4 eq. of NaH (50% in mineral oil). The temperature was slowly raised to room temperature and stirring continued, until thin layer chromatographie indicated the absence of starting material (1.5 h). After quenching with crushed ice, the product was extracted with ether, washed with water, dried over sodium sulfate and the solvents removed. Flash chromatography ($SiO_2$, hexane/ethylacetate=95/5) delivered 151 mg of the title compound as colourless oil.

e] (Z)-(1R,3S)-5-((2E,9E)-12,12,12-Trifluoro-11-trifluoromethyl-11-hydroxy-7,7-dimethyl-dodec-2,9-dienylidene)-4-methylene-cyclohexane-1,3-diol 0.83 g of tetrabutylammoniumfluoride trihydrate (2.60 mmol) in 3.5 ml of tetrahydrofuran was carefully dried by stirring during 2 h at room temperature over 1.05 g of 3 Å molecular sieve. This solution was then added to the above prepared 151 mg of (3E,10E)-12-[(Z)-(3S,5R)-3,5-bis-(tert-butyl-dimethyl-silanyloxy)-2-methylene-cyclohexylidene]-1,1,1-trifluoro-6,6-dimethyl-2-trifluoromethyl-dodeca-3,10-dien-2-ol and kept for 1.5 h at 45°. The reaction mixture was then poured onto crushed ice, extracted twice with ether, washed with water, dried over sodium sulfate and evaporated to dryness. Flash chromatography ($SiO_2$, hexane/ethylacetate=4/6) yielded 76 mg of the title compound as colourless oil.

MS: $(M)^+$ 456, $(M-H_2O)^+$ 438.

IR ($cm^{-1}$): 3360, 2980, 1308, 1294, 1211, 1179, 1146, 959.

NMR: (1H, δ, TMS) 0.86 (s, 6H), 1.3–2.2 (m, 9H+3OH), 2.29(dd, 1H), 2.45 (t, 1H), 2.57 (dd, 1H), 4.24 (m, 1H), 4.43 (br t, 1H), 5.00 (br s, 1H), 5.31 (br s, 1H), 5.55 (br d, 1H, J=16), 5.71 (dt, 1H), 6.03 (br d, 1H), 6.29 (dt, 1H), 6.38 (dd, 1H).

EXAMPLE 4

Preparation of (1R,3R)-5-[(2E,9E)-12,12,12-Trifluoro-11-trifluoromethyl-11-hydroxy-7,7-dimethyl-dodeca-2,9-dienylidene]-cyclohexane-1,3-diol a] E)-10,10,10-Trifluoro-9-trifluoromethyl-5,5-dimethyl-9-trimethylsilanyloxy-dec-7-enal 245 mg of (E)-10,10,10-Trifluoro-9-trifluoromethyl-9-hydroxy-5,5-dimethyl-dec-7-enal (0.765 mmol) (see example 3 c]) was dissolved in 3.6 ml of $CH_2Cl_2$ and treated successively at 0° with 9.3 mg of dimethylaminopyridine (0.1 eq.), 0.853 ml of triethylamine (8 eq.), and 0.581 ml of $(CH_3)_3SiCl$ (6 eq.). After stirring for 30 Min. at ambient temperature, the reaction mixture was poured onto crushed ice/ether, the organic layer washed with water, dried over sodium sulfate and evaporated to dryness. Flash chromatography ($SiO_2$, hexane/ethylacetate=95/5) delivered 275 mg of the very labile title compound as pale yellow oil.

b] (1R,3R)-5-[(2E,9E)-12-Trifluoro-11-trifluoromethyl-11-hydroxy-7,7-dimethyl-dodeca-2,9-dienylidene1-cyclohexane-1,3-diol 0.633 g of carefully dried (3R,5R)-[2-[3,5-bis-(t-butyldimethyl-silanyloxy)-cyclohexylidene]-ethyl]-diphenyl-phosphine oxide (*Tetrahedron Lett.* 32, 7663 (1991)) (1.6 eq.) was dissolved in 6 ml of abs. tetrahydrofuran and treated at −78° with 1.15 ml of secButyllithium (1.3M, cyclohexane). After 20 Min., 272 mg of (E)-10,10,10-Trifluoro-9-trifluoromethyl-5,5-dimethyl-9-trimethylsilanyloxy-dec-7-enal, dissolved in 2 ml of abs. tetrahydrofurane, was added to the deep red solution. The mixture was kept for 1 h at −78° and then quenched with $NH_4Cl$ solution. Twofold extraction with ether, washing with water, drying over sodium sulfate and evaporation of the solvents left a crude product which was purified by a short flash chromatography ($SiO_2$, hexane/ethylacetate=7/3) to give 580 mg of diastereomeric β-hydroxy-phosphine oxides as white foam which was processed as follows:

This intermediate was dissolved in 6 ml of abs. tetrahydrofuran and treated at 0° with roughly 4 eq. of NaH (50% in mineral oil). The temperature was slowly raised to room temperature and stirring continued, until thin layer chromatography indicated the absence of starting material (1.5 h). After quenching with crushed ice/$NH_4Cl$, the product was extracted with ether, washed with water, dried over sodium sulfate and the solvents removed. Flash chromatography ($SiO_2$, hexane/ethylacetate=95/5) gave 273 mg of triene as colourless oil which was deprotected as follows:

1.40 g of tetrabutylammoniumfluoride trihydrate (4.45 mmol) in 6 ml of tetrahydrofuran was carefully dried by stirring during 2 h at room temperature over 1.78 g of 3 Å molecular sieve. This solution was then added to the above prepared 270 mg of (1R,3R)-1,3-bis-(tert-butyl-dimethyl-silanyloxy)-5-((2E,9E)-12,12,12-trifluoro-7,7-dimethyl-11-trifluoromethyl-11-trimethylsilanyloxy-dodeca-2,9-dienylidene)-cyclohexane (0.371 mmol) and kept for 1.5 h at 40°. The reaction mixture was then poured onto crushed ice/$NH_4Cl$, extracted twice with ether, washed with water, dried over sodium sulfate and evaporated to dryness. Flash chromatography ($SiO_2$, hexane/ethylacetate=25/75) yielded 165 mg of the title compound as colourless oil. Typically, this product is contaminated with small amounts of 2Z-isomer which can be removed by HPLC.

MS: $(M)^+$ 444, $(M-H_2O)^+$ 426.

NMR: (1H, δ, TMS) 0.87 (s, 6H), 1.2–2.7 (m, 14H+3OH), 4.10 (m, 2H), 5.54 (d, 1H, J=15.5), 5.67 (dt, 1H), 6.00 (br d, 1H), 6.2–6.4 (m, 2H).

EXAMPLE 5

Preparation of (1R,3R)-5-[(2E)-12,12,12-Trifluoro-11-hydroxy-7,7-dimethyl-11-trifluoromethyl-dodec-2-enylidene)-cyclohexane-1,3-diol a] 10,10,10-Trifluoro-9-trifluoromethyl-5,5-dimethyl-decane-1,9-diol 1.00 g of 10,10,10-Trifluoro-9-trifluoromethyl-5,5-dimethyl-dec-7-ene-1,9-diol (3.12 mmol) (example 1 k]) was hydrogenated over 1 g of Pd/C (10%) at 9 bar $H_2$ pressure and room temperature for 20 h. Filtration over a pad of Celite and evaporation of the solvents left 0.83 g of the title compound which was used as such for the next step.

NMR: (1H, δ, TMS) 0.81 (s, 6H), 1.1–1.5 (m, 10H+OH), 1.80 (br t, 2H), 3.38 (t, 2H), 7.71 (s, 1H).

b] 10,10,10-Trifluoro-9-trifluoromethyl-9-hydroxy-5,5-dimethyl-decanal 830 mg of 10,10,10-Trifluoro-9-trifluoromethyl-5,5-dimethyl-decane-1,9-diol (2.56 mmol) was oxidized by reaction with 3.64 g of pyridinium-dichromate (3.8 eq.) in 79 ml of $CH_2Cl_2$ at room temperature over night. Filtration over a pad of silica gel, removal of the solvent and flash chromatography ($SiO_2$, hexane/ethylacetate=8/2) furnished 675 mg of the title compound as colourless oil.

NMR: (1H, δ, TMS) 0.83 (s, 6H), 1.05–1.2 (m, 4H), 1.3–1.55 (m, 4H), 1.80 (br t, 2H), 2.40 (br t, 2H), 7.71 (s, 1H), 9.66 (br s, 1H).

c] 10,10,10-Trifluoro-9-trifluoromethyl-5,5-dimethyl-9-trimethylsilanyloxy-decanal 672 mg of 10,10,10-Trifluoro-9-trifluoromethyl-9-hydroxy-5,5-dimethyl-decanal (2.085 mmol) was dissolved in 10 ml of $CH_2Cl_2$ and treated successively at 0° with 26 mg of dimethylaminopyridine (0.1 eq.), 2.32 ml of $NEt_3$ (8 eq.), and 1.58 ml of $(CH_3)_3SiCl$ (6 eq.). After stirring for 30 Min. at ambient temperature, the reaction mixture was quenched by pouring onto crushed ice/ether, the organic layer was washed with water, dried over sodium sulfate and evaporated to dryness. Flash chromatography ($SiO_2$, hexane/ethylacetate=96/4) delivered 717 mg of the labile title compound as pale yellow oil.

NMR: (1H, δ, TMS) 0.19 (s, 9H), 0.83 (s, 6H), 1.05–1.55 (m, 8H), 1.85 (br t, 2H), 2.39 (br t, 2H), 9.64 (br s, 1H).

d] (1R,3R)-5-[(2E)-12,12,12-Trifluoro-11-hydroxy-7,7-dimethyl-11-trifluoromethyl-dodec-2-enylidene)-cyclohexane-1,3-diol 0.709 g of carefully dried (3R,5R)-[2-[3,5-bis-(t-butyldimethyl-silanyloxy)-cyclohexylidene]-ethyl]-diphenyl-phosphine oxide (*Tetrahedron Lett.* 32, 7663 (1991)) (1.4 eq.) was dissolved in 5 ml of abs. tetrahydrofuran and treated at −78° with 1.325 ml of secButyllithium (1.3M, cyclohexane). After 20 Min. at this temperature, 347 mg of 10,10,10-trifluoro-9-trifluoromethyl-5,5-dimethyl-9-trimethylsilanyloxy-decanal (0.880 mmol), dissolved in 2 ml of abs. tetrahydrofurane, was added to the deep red solution. The mixture was kept for 1.5 h at −78° and then quenched with $NH_4Cl$ solution. Twofold extraction with ether, washing with water, drying over sodium sulfate and evaporation of the solvents left a crude product which was purified by a short flash chromatography ($SiO_2$, hexanel ethylacetate=7/3) to give 725 mg of diastereomeric β-hydroxy-phosphine oxides which was processed as follows:

This intermediate was dissolved in 6.1 ml of abs. tetrahydrofuran and treated at 0° with roughly 4 eq. of NaH (50% in mineral oil). The temperature was slowly raised to room temperature and stirring continued for 1 h. After quenching with crushed ice/$NH_4Cl$, the product was extracted twice with ether, washed with water, dried over sodium sulfate and the solvents removed. Flash chromatography ($SiO_2$, hexanel ethylacetate=96/4) gave 285 mg of triene as yellowish oil which was deprotected as follows:

1.50 g of tetrabutylammoniumfluoride trihydrate (4.76 mmol) in 6.5 ml of tetrahydrofuran was carefully dried by stirring during 2 h at room temperature over 1.91 g of 3 Å molecular sieve. This solution was then added to the above prepared 283 mg of (1R,3R)-1,3-bis-(tert-butyl-dimethylsilanyloxy)-5-((E)-12,12,12-trifluoro-7,7-dimethyl-11-trifluoromethyl-11-trimethylsilanyloxy-dodec-2-enylidene)-cyclohexane (0.378 mmol) and kept for 2 h at 40°. The reaction mixture was then poured onto crushed ice/NH$_4$Cl, extracted twice with ether, washed with water, dried over sodium sulfate and evaporated to dryness. Flash chromatography (SiO$_2$, hexane/ethylacetate=1/1) delivered 177 mg of the title compound as colourless oil. Typically, this product is contaminated with small amounts of Z-isomer which can be removed by HPLC.

MS: (M)$^+$ 446, (M–H$_2$O)$^+$ 428.

IR (cm$^{-1}$): 3345, 2958, 1628, 1470, 1366, 1213, 1180, 1142, 1047, 967, 936.

NMR: (1H, δ, TMS) 0.85 (s, 6H), 1.1–2.4 (m, 16H+2OH), 3.75 (br s, OH), 2.47 (dd, 1H), 2.63 (dd, 1H), 4.07 (m, 2H), 5.70 (dt, 1H), 6.01 (d, 1H), 6.26 (br dd, 1H).

EXAMPLE 6

(Z)-(1R,3S)-5-[(2E)-12,12,12-Trifluoro-11-hydroxy-7,7-dimethyl-11-trifluoromethyl-dodec-2-enylidene]-4-methylene-cyclohexane-1,3-diol was prepared in analogy to example 5 but using in step d] (Z)-(3S,5R)-[2-[3,5-bis-(t-butyldimethyl-silanyloxy)-2-methylene-cyclohexylidene]-ethyl]-diphenyl-phosphine oxide.

MS: (M)$^+$ 458, (M–H$_2$O)$^+$ 440.

IR (cm$^{-1}$): 3348, 2958, 1640, 1470, 1367, 1212, 1178, 1143, 1049, 976, 923.

NMR: (1H, δ, TMS) 0.84 (s, 6H), 1.15–2.1 (m, 12H+2OH), 1.97 (t, 2H), 2.26 (dd, 1HO, 2.59 (dd, 1H), 3.37 (br s, OH), 4.23 (m, 1H), 4.43 (m, 1H), 5.00 (br s, 1H), 5.31 (br s, 1H), 5.73 (dt, 1H), 6.03 (d, 1H), 6.38 (br dd, 1H).

EXAMPLE 7

(E)-(1R,3R)-5-[12,12,12-Tifluoro-11-hydroxy-7,7-dimethyl-11-trifluoromethyl-dodec-2-en-9-ynylidene]-cyclohexane-1,3-diol was prepared as described in example 1 but skipping the hydrogenation step l] as colourless oil.

Cl-MS: (M+NH$_4$)$^+$ 460.

NMR: (1H, δ, TMS) 0.96 (s, 6H), 1.2–2.6 (m, 12H+3OH), 2.16 (s, 2H), 4.11 (m, 2H), 5.66 (dt, 1H), 6.03 (d, 1H), 6.27 (br dd, 1H).

EXAMPLE 8

(Z)-(1R,3S)-4-Methylene-5-[(E)-12,12,12-tifluoro-11-hydroxy-7,7-dimethyl-11-trifluoromethyl-dodec-2-en-9-ynylidene]-cyclohexane-1,3-diol was prepared as described in example 1 but skipping the hydrogenation step l] and using in step o] (Z)-(3S,5R)-[2-[3,5-bis-(t-butyldimethyl-sianyloxy)-2-methylene-cyclohexylidene]-ethyl]-diphenyl-phosphine oxide, respectively, as colourless oil.

MS: (M)$^+$ 454, (M–H$_2$O)$^+$ 436.

NMR: (1H, δ, TMS) 0.95 (s, 6H), 1.2–1.5 (m, 4H+2OH), 1.9–2.2 (m, 4H), 2.15 (s, 2H), 2.26 (dd, 1H), 2.60 (dd, 1H), 4.23 (m, 1H), 4.46 (m, 1H), 5.01 (br s, 1H), 5.31 (br s, 1H), 5.73 (dt, 1H), 6.04 (d, 1H), 6.38 (br dd, 1H).

EXAMPLE 9

(Z)-(S)-4-Methylene-3-[(E)-12,12,12-tifluoro-11-hydroxy-7,7-dimethyl-11-trifluoromethyl-dodec-2-en-9-ynylidene]-cyclohexane-1-ol was prepared as described in example 1 but skipping the hydrogenation step l] and using in step o] (Z)-(5S)-[2-[5-(t-butyldimethyl-silanyloxy)-2-methylene-cyclohexylidene]-ethyl]-diphenyl-phosphine oxide, respectively, as colourless oil.

MS: (M)$^+$ 438, (M–H$_2$O)$^+$ 420.

NMR: (1H, δ, TMS) 0.96 (s, 6H), 1.2–2.5 (m, 1 H+2OH), 2.15 (s, 2H), 2.54 (dd, 1H), 3.96 (m, 1H), 4.83 (br s, 1H), 5.05 (br s, 1H), 5.67 (dt, 1H), 5.89 (d, 1H), 6.39 (br dd, 1H).

EXAMPLE 10

Preparation of (10E,12Z)-(S)-12-(5-Hydroxy-2-methylene-cyclohexylidene)-6,6-dimethyl-2-methyl-dodec-10-en-3-yn-2-ol a] 2,6,6-Trimethyl-10-(tetrahydro-pyran-2-yloxy)-dec-3-yn-2-ol 3.01 g of 2-(8,8-Dibromo-5,5-dimethyl-oct-7-enyloxy)-tetrahydro-pyrane (11.44 mmol) (example 1/step i]) was dissolved in 33 ml of abs. tetrahydrofuran and treated at −78° with 15.12 ml of n-butyllithium (1.5 M, hexane, 3 eq.). 50 Min. later, 2.77 ml of acetone (5 eq.), dissolved in 10 ml of tetrahydrofurane, was added dropwise and the mixture kept for 30 Min. at −78°. Warming to ambient temperature, pouring onto crushed ice, twofold extraction with ether, washing with water, drying over sodium sulfate and evaporation of the solvents left a crude product which was purified by flash chromatography (SiO$_2$, hexane/ethylacetate=85/15) to yield 2.02 g of the title compound as colorless oil.

MS: (M–CH$_3$)$^+$ 281.

b] 5,5,9-Trimethyl-dec-7-ene-1,9-diol 609 mg of 2,6,6-Trimethyl-10-(tetrahydro-pyran-2-yloxy)-dec-3-yn-2-ol (2.05 mmol) was dissolved in 13.5 ml of methanol, treated with 76 mg of pyridinium-(toluene-4-sulfonate) (0.15 eq.), and kept at room temperature for 1 night. The reaction mixture was then poured onto crushed ice/Na$_2$CO$_3$, extracted twice with ethylacetate, washed with brine, dried over sodium sulfate and evaporated to dryness. Flash chromatography (SiO$_2$, hexane/ethylacetate=7/3) produced 413 mg of the title compound as yellowish oil.

MS: (M–CH$_3$)$^+$ 197.

NMR: (1H, δ, TMS) 0.94 (s, 6H), 1.51 (s, 6H), 1.2–1.6 (m, 6H), 1.63 (br s, 2 OH), 2.06 (s, 2H), 3.68 (t, 2H).

c] 9-Hydroxy-5,5,9-trimethyl-dec-7-ynal 410 mg of 5,5,9-Trimethyl-dec-7-ene-1,9-diol (1.93 mmol) ) was oxidized by reaction with 2.76 g of pyridinium-dichromate (3.8 eq.) in 61 ml of CH$_2$Cl$_2$ at room temperature over night. Filtration over a pad of Celite, removal of the solvent and flash chromatography (SiO$_2$, hexane/ethylacetate=8/2) furnished 245 mg of the title compound as colourless oil.

NMR: (1H, δ, TMS) 0.95 (s, 6H), 1.30 (m, 2H), 1.51 (s, 6H), 1.58 (m, 2H+OH), 2.07 (s, 2H), 2.44(td, 2H), 9.78 (t, 1H).

MS: (M–CH$_3$)$^+$ 195.

d] 5,5,9-Trimethyl-9-trimethylsilanyloxy-dec-7-ynal 242 mg of 9-Hydroxy-5,5,9-trimethyl-dec-7-ynal (1.15 mmol) was dissolved in 14 ml of CH$_2$Cl$_2$ and treated with 1.18 ml of 1-(trimethylsilyl)imidazole (7 eq.). After 20 h at room temperature, the mixture was poured onto crushed ice, extracted twice with ether, washed with water, dried over sodium sulfate and evaporated to dryness. Flash chromatography (SiO$_2$, hexane/ethylacetate=95/5) yielded 293 mg of the title compound as colourless oil.

CI-MS: (M+NH$_4$)$^+$ 300.

e] (10E,12Z)-(S)-12-(5-Hydroxy-2-methylene-cyclohexylidene)-6,6-dimethyl-2-methyl-dodec-10-en-3-yn-2-ol 0.577 g of carefully dried (Z)-(5S)-[2-[5-(t-butyldimethyl-silanyloxy)-2-methylene-cyclohexylidene]- ethyl]-diphenyl-phosphine oxide (1.27 mmol) was dissolved in 8.5 ml of abs. tetrahydrofuran and treated at −78° with 0.819 ml of n-butyllithium (1.55M, hexane). After 20 Min. at this temperature, 100 mg of 5,5,9-trimethyl-9-trimethylsilanyloxy-dec-7-ynal (0.354 mmol), dissolved in 2 ml of abs. tetrahydrofurane, was added to the deep red solution. The mixture was kept for 1 h at −78° and 30 Min. at −20° and then quenched with $NH_4Cl$-solution. Twofold extraction with ether, washing with brine, drying over sodium sulfate and evaporation of the solvents left a crude product which was purified by a short flash chromatography ($SiO_2$, hexane/ethylacetate=7/3) to give 196 mg of diastereomeric β-hydroxy-phosphine oxides which was processed as follows:

This intermediate was dissolved in 2.4 ml of abs. tetrahydrofuran and treated at 0° with roughly 4 eq. of NaH (50% in mineral oil). The temperature was slowly raised to room temperature and stirring continued for 1 h. After quenching with crushed ice/$NH_4Cl$, the product was extracted twice with ether, washed with $NH_4Cl$, dried over sodium sulfate and the solvents removed. Flash chromatography ($SiO_2$, hexane/ethylacetate=98.5/1.5) gave 81 mg of triene as colourless oil which was deprotected as follows:

MS: $(M)^+$ 516, $(M-CH_3)^+$ 501.

0.776 g of Tetrabutylammoniumfluoride trihydrate (2.46 mmol) in 2.5 ml of tetrahydrofuran was carefully dried by stirring during 1.5 h at room temperature over 0.98 g of 3 Å molecular sieve. This solution was then added to the above prepared 81 mg (0.157 mmol) and kept for 2 h at 40°. The reaction mixture was then poured onto crushed ice/$NH_4Cl$, extracted twice with ethylacetate, washed with brine, dried over sodium sulfate and evaporated to dryness. Flash chromatography ($SiO_2$, hexane/ethylacetate=7/3) gave 39 mg of the title compound as colourless oil. Typically, this product is contaminated with small amounts of 10Z-isomer which can be removed by HPLC.

NMR: (1H, δ, TMS) 0.92 (s, 6H), 1.2–2.5 (m, 11H+2OH), 1.50 (s, 6H), 2.04 (s, 2H), 2.53 (dd, 1H), 3.91 (m, 1H), 4.83 (br s, 1H), 5.05 (br s, 1H), 5.68 (dt, 1H), 5.89 (d, 1H), 6.41 (dd, 1H).

MS: $(M-H_2O)^+$ 312, $(M-H_2O-CH_3)^+$ 297.

EXAMPLE 11

Preparation of (10E)-(3R,5R)-12-(3,5-Dihydroxy-cyclohexylidene)-6,6-dimethyl-2-methyl-dodec-10-en-3-yn-2-ol In analogy to example 10, but using in step e] (3R,5R)-[2-[3,5-bis-(t-butyldimethyl-silanyloxy)-cyclohexylidene]-ethyl]-diphenyl-phosphine oxide was prepared (10E)-(3R, 5R)-12-(3,5-Dihydroxy-cyclohexylidene)-6,6-dimethyl-2-methyl-dodec-10-en-3-yn-2-ol as yellowish oil.

NMR: (1H, δ, TMS) 0.93 (s, 6H), 1.2–2.4 (m, 10H+3OH), 1.50 (s, 6H), 2.04 (s, 2H), 2.48 (dd, 1H), 2.63 (dd, 1H), 4.09 (m, 2H), 5.68 (dt, 1H), 5.99 (d, 1H), 6.27 (dd, 1H).

MS: $(M-H_2O)^+$ 316, $(M-H_2O-CH_3)^+$ 301.

EXAMPLE 12

Preparation of (Z)-(1S)-3-[(2E)-11-Hydroxy-7,7,11-trimethyl-dodeca-2-en-ylidene]-4-methylene-cyclohexane-1-ol a] 5,5,9-Trimethyl-decane-1,9-diol 667 mg of 5,5,9-Trimethyl-dec-7-ene-1,9-diol (3.14 mmol) (example 10/step b]) was dissolved in 30 ml of ethylacetate containing one drop of triethylamine (in order to avoid elimination of water) and hydrogenated over 300 mg of Pd/C(5%) at room temperature and atmospheric pressure during 180 Min. The reaction mixture was filtered over a pad of Celite and the solvents removed to leave 620 mg of the title compound as colourless oil, used as such for the next step.

NMR: (1H, δ, TMS) 0.85 (s, 6H), 1.1–1.6 (m, 12H+2OH), 1.22 (s, 6H), 3.63 (t, 2H).

MS: $(M-CH_3)^+$ 201, $(M-HO)^+$ 199.

b] 9-Hydroxy-5,5,9-trimethyl-decanal 660 mg of 5,5,9-Trimethyl-decane-1,9-diol (3.05 mmol) was oxidized by reaction with 4.36 g of pyridinium-dichromate (3.8 eq.) in 97 ml of $CH_2Cl_2$ at room temperature over night. Filtration over a pad of silica gel, removal of the solvent and flash chromatography ($SiO_2$, hexane/ethylacetate=7/3) furnished 452 mg of the title compound as colourless oil.

NMR: (1H, δ, TMS) 0.87 (s, 6H), 1.1–1.7 (m, 10H+OH), 1.22 (s, 6H), 2.41(td, 2H), 9.77 (t, 1H).

MS: $(M-CH_3)^+$ 199.

c] 5,5,9-Trimethyl-9-trimethylsilanyloxy-decanal 450 mg of 9-Hydroxy-5,5,9-trimethyl-decanal (2.10 mmol) was dissolved in 26 ml of $CH_2Cl_2$ and treated with 2.15 ml of 1-(trimethylsilyl)imidazole (7 eq.). After 20 h at room temperature, the mixture was poured onto crushed ice, extracted twice with ether, washed with water, dried over sodium sulfate and evaporated to dryness. This crude product turned out to be a mixture of desired aldehyde and the corresponding semi-animal, formed by nucleophilic addition of imidazole. The latter was cleaved by dissolving in 50 ml of hexane/ethylacetate=9/1 and stirring for 2.5 h over 15 g of silica gel. Filtration, evaporation of the solvents and flash chromatography ($SiO_2$, hexane/ethylacetate=97/3) yielded 566 mg of the title compound as colourless oil.

NMR: (1H, δ, TMS) 0.10 (s, 9H), 0.86 (s, 6H), 1.1–1.7 (m, 10H), 1.20 (s, 6H), 2.40(td, 2H), 9.77 (t, 1H).

MS: $(M-CH_3)^+$ 271.

d] (Z)-(1S)-3-[(2E)-11-Hydroxy-7,7,11-trimethyl-dodeca-2-en-ylidene]-4-methylene-cyclohexane-1-ol 0.483 g of carefully dried (Z)-(5S)-[2-[5-(t-butyldimethyl-silanyloxy)-2-methylene-cyclohexylidene]-ethyl]-diphenyl-phosphine oxide(1.07 mmol) was dissolved in 5 ml of abs. tetrahydrofuran and treated at −78° with 0.800 ml of n-butyllithium (1.55M, hexane). After 20 Min. at this temperature, 181 mg of 5,5,9-trimethyl-9-trimethylsilanyloxy-decanal (0.632 mmol), dissolved in 2 ml of abs. tetrahydrofurane, was added to the deep red solution. The mixture was kept for 40 Min. at −78° and then quenched with $NH_4Cl$-solution. Twofold extraction with ethylacetate, washing with brine, drying over sodium sulfate and evaporation of the solvents left a crude product which was purified by a short flash chromatography ($SiO_2$, hexane/ethylacetate=7/3) to give 466 mg of diastereomeric β-hydroxy-phosphine oxides which was processed as follows:

This intermediate was dissolved in 6 ml of abs. tetrahydrofuran and treated at 0° with roughly 4 eq. of NaH (50% in mineral oil). The temperature was slowly raised to room temperature and stirring continued for 40 Min. After quenching with crushed ice/$NH_4Cl$, the product was extracted twice with ether, washed with brine, dried over sodium sulfate and the solvents removed. Flash chromatography ($SiO_2$, hexane/ethylacetate=99/1) afforded 198 mg of triene as colourless oil which was deprotected as follows:

MS: $(M)^+$ 520.

1.88 g of tetrabutylammoniumfluoride trihydrate (5.96 mmol) in 6 ml of tetrahydrofuran was carefully dried by stirring during 2 h at room temperature over 2.38 g of 3 Å molecular sieve. This solution was then added to the above prepared 198 mg (0.38 mmol) and kept for 2 h at 40°. The reaction mixture was then poured onto crushed ice, extracted twice with ethylacetate, washed with brine, dried over sodium sulfate and evaporated to dryness. Flash chromatography (SiO$_2$, hexane/ethylacetate=4/6) gave 120 mg of the title compound as colourless oil. Typically, this product is contaminated with small amounts of 2Z-isomer which can be removed by HPLC.

NMR: (1H, δ, TMS) 0.83 (s, 6H), 1.10–2.5 (m, 17H+2OH), 1.22 (s, 6H), 2.53 (dd, 1H), 3.91 (m, 1H), 4.83 (br s, 1H), 5.05 (br s, 1H), 5.68 (dt, 1H), 5.89 (d, 1H), 6.40 (dd, 1H).

MS: (M)$^+$ 334, (M–H$_2$O)$^+$ 316, (M–2H$_2$O)$^+$ 298.

IR (cm$^{-1}$): 3362, 2937, 2867, 1635, 1470, 1364, 1053.

EXAMPLE 13

Preparation of (Z)-(1R,3S)-5-[(E)-11-Hydroxy-7,7,11-trimethyl-dodec-2-enylidene]-4-methylene-cyclohexane-1,3-diol In analogy to example 12, but using in step d] (Z)-(3S,5R)-[2-[3,5-bis-(t-butyldimethyl-silanyloxy)-2-methylene-cyclohexylidene]-ethyl]-diphenyl-phosphine oxide was prepared (Z)-(1R,3S)-5-[(E)-11-Hydroxy-7,7,11-trimethyl-dodec-2-enylidene]-4-methylene-cyclohexane-1,3-diol as colourless oil.

NMR: (1H, δ, TMS) 0.84 (s, 6H), 1.10–2.15 (m, 14H+3OH), 1.22 (s, 6H), 2.26 (dd, 1H), 2.57 (dd, 1H), 4.23 (m, 1H), 4.43 (m, 1H), 5.01 (br s, 1H), 5.31 (br s, 1H), 5.74 (dt, 1H), 6.03 (d, 1H), 6.38 (dd, 1H).

MS: (M–H$_2$O)$^+$ 332, (M–2H$_2$O)$^+$ 314.

EXAMPLE 14

Preparation of (2E)-(1R,3R)-5-(11-Hydroxy-7,7,11-trimethyl-dodeca-2-enylidene)-cyclohexane-1,3-diol In analogy to example 12, but using in step d] (3R,5R)-[2-[3,5-bis-(t-butyldimethyl-silanyloxy)-cyclohexylidene]-ethyl]-diphenyl-phosphine oxide was prepared (2E)-(1R,3R)-5-(11-Hydroxy-7,7,11-trimethyl-dodeca-2-enylidene)-cyclohexane-1,3-diol as colourless oil.

NMR: (1H, δ, TMS) 0.84 (s, 6H), 1.10–2.3 (m, 16H+3OH), 1.22 (s, 6H), 2.47 (dd, 1H), 2.63 (dd, 1H), 4.09 (m, 2H), 5.68 (dt, 1H), 5.99 (d, 1H), 6.26 (dd, 1H).

MS: (M–H$_2$O)$^+$ 320, (M–2H$_2$O)$^+$ 302.

EXAMPLE 15

Preparation of (1R,3R)-5-[(2E,9E)-11-Hydroxy-7,7,11-trimethyl-dodeca-2,9-dien-ylidene]-cyclohexane-1,3-diol a] 5,5-Dimethyl-oct-7-yn-1-ol 5.04 g of 2-(8,8-Dibromo-5,5-dimethyl-oct-7-enyloxy)-tetrahydro-pyrane (example1/step i]) (12.66 mmol) was dissolved in 55 ml of abs. tetrahydrofuran and treated at −78° with 25.3 ml of n-butyllithium (1.5 M, hexane, 3 eq.). 30 Min. later, the reaction mixture was poured onto crushed ice/NH$_4$Cl, extracted twice with ether, washed with brine, dried over sodium sulfate and evaporated to dryness. Flash chromatography (SiO$_2$, hexane/ethylacetate=95/5) gave 3.07 g of 2-(5,5-dimethyl-oct-7-ynyloxy)-tetrahydro-pyrane which was deprotected as follows: 2.00 g thereof (8.39 mmol) was dissolved in 57 ml of methanol, treated with 211 mg of pyridinium-(toluene-4-sulfonate) (0.1 eq.), and kept at room temperature for 1 night. The reaction mixture was then poured onto crushed ice/Na$_2$CO$_3$, extracted twice with ether, washed with water, dried over sodium sulfate and evaporated to dryness. Flash chromatography (SiO$_2$, pentane/methylacetate=75/25) gave 1.27 g of the title compound as colourless oil, 99% pure according to GC.

NMR: (1H, δ, TMS) 0.96 (s, 6H), 1.30–1.6 (m, 6H+OH), 1.98 (t, 1H), 2.07 (d, 2H), 3.67 (t, 2H).

MS: (M–C$_3$H$_3$)$^+$ 115.

b] 5,5,9-Trimethyl-dec-7-yne-1,9-diol

To a solution of 1.27 g of 5,5-dimethyl-oct-7-yn-1-ol (8.213 mmol) in 16 ml of abs. tetrahydrofuran and 6.6 ml of 1,3-dimethyl3,4,5,6-tetrahydro-2-(1H)-pyrimidinone (DMPU) was added at −78° 15.93 ml of n-butyllithium (1.55 M, hexane, 3 eq.). The internal temperature was allowed to reach −20° before, again at −78°, 2.42 ml of acetone (4 eq.), dissolved in 5 ml of tetrahydrofurane, was added dropwise, and the mixture was kept for 10 Min. at −78°. Warming to ambient temperature, pouring onto crushed ice/NH$_4$Cl-solution, twofold extraction with ether, washing with brine, drying over sodium sulfate and evaporation of the solvents left a crude product which was purified by flash chromatography (SiO$_2$, hexane/ethylacetate=7/3 to 1/1) to yield 0.75 g of starting material and 767 mg of the title compound as colorless oil.

NMR: (1H, δ, TMS) 0.94 (s, 6H), 1.30–1.7 (m, 6H+2OH), 1.51 (s, 6H), 2.06 (s, 2H), 3.68 (t, 2H).

MS: (M–CH$_3$)$^+$ 197.

c] (E)-9-Hydroxy-5,5,9-trimethyl-dec-7-enal 433 mg of LiAlH$_4$ (5 eq.) was suspended in 40 ml of abs. tetrahydrofuran and cooled down to 0°. 614 mg of sodium methylate (5 eq.) was added, followed by a solution of 485 mg of 5,5,9-trimethyl-dec-7-yne-1,9-diol (2.284 mmol), dissolved in 27 ml of tetrahydrofurane. The mixture was heated to reflux for 2.5 h and then, at 0°, carefully quenched with 3.6 ml of water and 3.6 ml of 2N NaOH. 62 ml of ether was then added and the mixture vigorously stirred during 20 Min. to complete hydrolysis of the Al-salts. Careful drying over magnesium sulfate and evaporation of the solvents left 481 mg of (E)-5,5,9-trimethyl-dec-7-ene-1,9-diol which was further processed as follows:

It was oxidized by stirring over 3.20 g of pyridinium-dichromate (3.8 eq.) in 71 ml of CH$_2$Cl$_2$ at room temperature over night. Filtration over a pad of silica gel, removal of the solvent and flash chromatography (SiO$_2$, hexane/ethylacetate=8/2) furnished 233 mg of the title compound as colourless oil.

NMR: (1H, δ, TMS) 0.86 (s, 6H), 1.20 (m, 2H), 1.32 (s, 6H), 1.5–1.7 (m, 2H+OH), 1.93 (m, 2H), 2.41(td, 2H), 5.61 (m, 2H), 9.76 (t, 1H).

MS: (M–CH$_3$)$^+$ 197, (M–H$_2$O)$^+$ 194.

d] (E)-5,5,9-Trimethyl-9-trimethylsilanyloxy-dec-7-enal 230 mg of (E)-9-Hydroxy-5,5,9-trimethyl-dec-7-enal (1.083 mmol) was dissolved in 13.5 ml of CH$_2$Cl$_2$ and treated with 1.11 ml of 1-(trimethylsilyl)imidazole (7 eq.). After 20 h at room temperature, the mixture was poured onto crushed ice, extracted twice with ether, washed with brine, dried over sodium sulfate and evaporated to dryness. Flash chromatography (SiO$_2$, hexane/ethylacetate=95/5) furnished 281 mg of the title compound as colourless oil.

NMR: (1H, δ, TMS) 0.10 (s, 9H), 0.86 (s, 6H), 1.20 (m, 2H), 1.30 (s, 6H), 1.5–1.7 (m, 2H), 1.91 (d, 2H), 2.41(td, 2H), 5.54 (m, 2H), 9.76 (t, 1H).

MS: (M)$^+$ 284, (M–CH$_3$)$^+$ 269.

e] (1R,3R)-5-1(2E,9E)-11-Hydroxy-7,7,11-trimethyl-dodeca-2,9-dien-ylidene]-cyclohexane-1,3-diol 0.712 g of carefully dried (3R,5R)-[2-[3,5-bis-(t-butyldimethyl-silanyloxy)-cyclohexylidene]-ethyl]- diphenyl-phosphine oxide (2.5 eq.) was dissolved in 8 ml of abs. tetrahydrofuran and treated at −78° with 0.920 ml of n-butyllithium (1.55M, hexane). After 10 Min., 0.142 g of (E)-5,5,9-trimethyl-9-trimethylsilanyloxy-dec-7-enal, dissolved in 2 ml of abs. tetrahydrofurane, was added dropwise to the deep red solution. The mixture was kept for 1 h at −78° and then quenched with NH$_4$Cl solution. Twice extraction with ether, washing with brine, drying over sodium sulfate and evaporation of the solvents left a crude product which was purified by short flash chromatography (SiO$_2$, hexane/ ethylacetate=7/3) to yield 0.324 g of diastereomeric β-hydroxy-phosphine oxides which was processed as follows:

This intermediate was dissolved in 3.5 ml of abs. tetrahydrofuran and treated at 0° with roughly 4.5 eq. of NaH (50% in mineral oil). The temperature was slowly raised to room temperature and stirring continued, until thin layer chromatography indicated the absence of starting material (1 h). After quenching with crushed ice/NH$_4$Cl, the product was extracted with ether, washed with brine, dried over sodium sulfate and the solvents removed. Flash chromatography (SiO$_2$, hexane/ethylacetate=98/2) yielded 151 mg of triene as colourless oil which was deprotected as follows:

MS: (M−CH$_3$)$^+$ 621.

1.15 g of tetrabutylammoniumfluoride trihydrate (3.64 mmol) in 3.6 ml of tetrahydrofuran was carefully dried by stirring during 1.5 h at room temperature over 1.56 g of 3 Å molecular sieve. This solution was then added to the above prepared intermediate (0.232 mmol) and kept for 2 h at 35–40°. The reaction mixture was then poured onto crushed ice, extracted twice with ethylacetate, washed with brine, dried over sodium sulfate and evaporated to dryness. Two successive flash chromatographies (SiO$_2$, ethylacetate; SiO$_2$, hexane/isopropanol=8/2) gave 79 mg of the title compound as colourless oil. Typically, this product is contaminated with small amounts of 2Z-isomer which can be removed by HPLC.

NMR: (1H, δ, TMS) 0.84 (s, 6H), 1.10–2.3 (m, 12H+ 3OH), 1.31 (s, 6H), 2.48 (dd, 1H), 2.63 (dd, 1H), 4.09 (m, 2H), 5.60 (m, 2H), 5.67 (dt, 1H), 5.99 (d, 1H), 6.27 (dd, 1H).

MS: (M−H$_2$O)$^+$ 318, (M−2H$_2$O)$^+$ 300.

IR (cm$^{-1}$): 3359, 2931, 2842, 1625, 1468, 1364, 1051, 974.

EXAMPLE 16

Preparation of (Z)-(S)-3-[(2E,9E)-11-Hydroxy-7,7, 11-trimethyl-dodeca-2,9-dien-ylidene]-4-methylene-cyclohexane-1-ol In analogy to example 15, but using in step e] (Z)-(5S)-[2-[5-(t-butyldimethyl-silanyloxy)-2-methylene-cyclohexylidene]-ethyl]-diphenyl-phosphine oxide was prepared (Z)-(S)-3-[(2E,9E)-11-Hydroxy-7,7,11-trimethyl-dodeca-2,9-dien-ylidenel-4-methylene-cyclohexane-1-ol as colourless oil.

NMR: (1H, δ, TMS) 0.83 (s, 6H), 1.10–2.5 (m, 13H+ 2OH), 1.31 (s, 6H), 2.53 (dd, 1H), 3.91 (m, 1H), 4.83 (br s, 1H), 5.05 (br s, 1H), 5.60 (m, 2H), 5.67 (dt, 1H), 5.88 (d, 1H), 6.40 (dd, 1H).

MS: (M)$^+$ 332, (M−H$_2$O)$^+$ 314.

IR (cm$^{-1}$): 3353, 2933, 2842, 1635, 1440, 1364, 1052.

What is claimed is:

1. A compound of the formula:

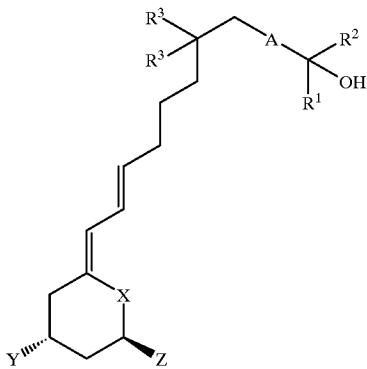

I wherein
X is C=CH$_2$ or CH$_2$;
Y and Z are independently of each other hydrogen, fluorine or hydroxy;
A is —C≡C—, —CH=CH— or —CH$_2$—CH$_2$—;
R$^1$ and R$^2$ are independently of each other alkyl or perfluoroalkyl; and
R$^3$ is lower alkyl.

2. The compound according to claim 1 wherein one of Y and Z is hydroxy and the other is fluorine or hydrogen.

3. The compound according to claim 2 wherein A is —C=C—.

4. The compound according to claim 3 wherein said compound is (Z)-(S)-3-[(2E,9E)-11-hydroxy-7,7,11-trimethyl-dodeca-2,9-dien-ylidene]-4-methylene-cyclohexane-1-ol.

5. The compound according to claim 1 wherein Y and Z are both hydroxy.

6. The compound according to claim 5 wherein A is —C=C—.

7. The compound according to claim 6 wherein said compound is (1R,3R)-5-[(2E,9Z)-12,12,12-trifluoro-11-hydroxy-7,7-dimethyl-11-trifluoromethyl-dodeca-2,9-dienylidene)-cyclohexane-1,3-diol.

8. The compound according to claim 6 wherein said compound is (Z)-(1R,3S)-4-methylene-5-[(2E,9Z)-12,12,12-trifluoro-11-hydroxy-7,7-dimethyl-11-trifluoromethyl-dodeca-2,9-dienylidene]-cyclohexane-1,3-diol.

9. The compound according to claim 6 wherein said compound is (Z)-(1R,3S)-5-((2E,9E)-12,12,12-trifluoro-11-trifluoromethyl-11-hydroxy-7,7-dimethyl-dodec-2,9-dienylidene)-4-methylene-cyclohexane-1,3-diol.

10. The compound according to claim 6 wherein said compound is (1R,3R)-5-[(2E,9E)-12,12,12-trifluoro-11-trifluoromethyl-11-hydroxy-7,7-dimethyl-dodeca-2,9-dienylidene]-cyclohexane-1,3-diol.

11. The compound according to claim 6 wherein said compound is (1R,3R)-5-[(2E,9E)-11-hydroxy-7,7,11-trimethyl-dodeca-2,9-dien-ylidene]-cyclohexane-1,3-diol.

12. The compound according to claim 1 wherein A is —CH$_2$CH$_2$—.

13. The compound of claim 12 wherein one of Y and Z are hydroxy and the other is fluorine or hydrogen.

14. The compound according to claim 13 wherein said compound is (Z)-(1S)-3-[(2E)-11-hydroxy-7,7,11-trimethyl-dodeca-2-en-ylidene]-4-methylene-cyclohexane-1-ol.

15. The compound according to claim 12 wherein Y and Z are both hydroxy.

16. The compound according to claim 15 wherein said compound is (1R,3R)-5-[(2E)-12,12,12-trifluoro-11-hydroxy-7,7-dimethyl-11-trifluoromethyl-dodec-2-enylidene)-cyclohexane-1,3-diol.

17. The compound according to claim 15 wherein said compound is (Z)-(1R,3S)-5-[(2E)-12,12,12-trifluoro-11-hydroxy-7,7-dimethyl-11-trifluoromethyl-dodec-2-enylidene]-4-methylene-cyclohexane-1,3-diol.

18. The compound according to claim 15 wherein said compound is (Z)-(1R,3S)-5-[(E)-11-hydroxy-7,7,11-trimethyl-dodec-2-enylidene]-4-methylene-cyclohexane-1,3-diol.

19. The compound according to claim 15 wherein said compound is (2E)-(1R,3R)-5-(11-hydroxy-7,7,11-trimethyl-dodeca-2-enylidene)-cyclohexane-1,3-diol.

20. The compound according to claim 2 wherein A is —C≡C—.

21. The compound according to claim 20 wherein said compound is (10E)-(3R,5R)-12-(3,5-dihydroxy-cyclohexylidene)-6,6-dimethyl-2-methyl-dodec-10-en-3-yn-2-ol.

22. The compound according to claim 20 wherein said compound is (Z)-(S)-4-methylene-3-[(E)-11-hydroxy-7,7-dimethyl-11,11-bis-trifluoromethyl-dodec-2-en-9-ynylidene]-cyclohexane-1-ol.

23. The compound according to claim 20 wherein said compound is (10E,12Z)-(S)-12-(5-hydroxy-2-methylene-cyclohexylidene)-6,6-dimethyl-2-methyl-dodec-10-en-3-yn-2-ol.

24. The compound according to claim 5 wherein A is —C≡C—.

25. The compound according to claim 24 wherein said compound is (E)-(1R,3R)-5-[11-hydroxy-7,7-dimethyl-11,11-bis-trifluoromethyl-dodec-2-en-9-ynylidene]-cyclohexane-1,3-diol.

26. The compound according to claim 24 wherein said compound is (Z)-(1R,3S)-4-ethylene-5-[(E)-11-hydroxy-7,7-dimethyl-11,11-bis-trifluoromethyl-dodec-2-en-9-ynylidene]-cyclohexane-1,3-diol.

27. A compound of the formula:

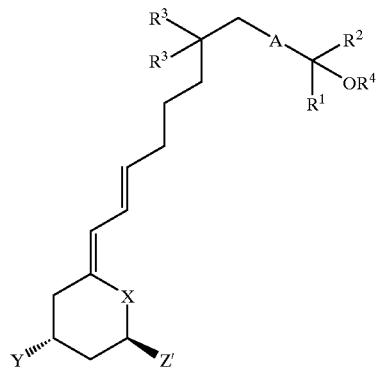

wherein

X is C=CH$_2$ or CH$_2$;

A is —C≡C—, —CH=CH— or —CH$_2$—CH$_2$—;

R$^1$ and R$^2$ are independently of each other alkyl or perfluoroalkyl;

R$^3$ is lower alkyl;

Y' and Z' are tert-butyldimethylsilyloxy or trimethylsilyloxy; and

R$^4$ is trimethylsilyl.

* * * * *

UNITED STATES PATENT AND TRADEMARK OFFICE
CERTIFICATE OF CORRECTION

PATENT NO. : 6,184,422 B1
DATED : February 6, 2001
INVENTOR(S) : Pierre Barbier, Franz Bauer, Peter Mohr, Marc Muller, Wolfgang Parson Page 1 of 1

Claim

It is certified that error appears in the above-identified patent and that said Letters Patent is hereby corrected as shown below:

Claim 26, Column 30, Line 2, delete "(Z)-(1R,3S)-4-ethylene-5-[(E)-11-hydroxy-7," and insert -- "(Z)-(1R,3S)-4-methylene-5-[(e)-11-hydroxy-7,--.

Claim 27, Column 30, Line 31, delete "tert-butyidimethylsilyloxy" and insert -- tert-butyldimethylsilyloxy--.

Signed and Sealed this

Fifth Day of June, 2001

Attest:

Attesting Officer

NICHOLAS P. GODICI
*Acting Director of the United States Patent and Trademark Office*